United States Patent
Ohuchi et al.

(10) Patent No.: US 9,865,082 B2
(45) Date of Patent: Jan. 9, 2018

(54) IMAGE PROCESSING SYSTEM, X-RAY DIAGNOSTIC APPARATUS, AND IMAGE PROCESSING METHOD

(71) Applicant: TOSHIBA MEDICAL SYSTEMS CORPORATION, Otawara-Shi (JP)

(72) Inventors: Hiroyuki Ohuchi, Otawara (JP); Shinichi Hashimoto, Otawara (JP); Takuya Sakaguchi, Utsunomiya (JP); Ko Fuchigami, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 233 days.

(21) Appl. No.: 14/664,139

(22) Filed: Mar. 20, 2015

(65) Prior Publication Data
US 2015/0193962 A1    Jul. 9, 2015

Related U.S. Application Data

(63) Continuation of application No. PCT/JP2013/075374, filed on Sep. 19, 2013.

(30) Foreign Application Priority Data

Sep. 20, 2012  (JP) ................. 2012-207492
Sep. 19, 2013  (JP) ................. 2013-194601

(51) Int. Cl.
G06T 15/10 (2011.01)
G06T 15/08 (2011.01)
(Continued)

(52) U.S. Cl.
CPC ............ *G06T 15/08* (2013.01); *A61B 6/4417* (2013.01); *A61B 6/4441* (2013.01); *A61B 6/487* (2013.01);
(Continued)

(58) Field of Classification Search
CPC . G06T 15/08; G06T 7/70; G06T 11/60; G06T 2207/10116; G06T 2207/10132;
(Continued)

(56) References Cited

U.S. PATENT DOCUMENTS

2007/0038058 A1*  2/2007  West ............... A61N 5/1049
                                                600/407
2007/0049817 A1*  3/2007  Preiss ............. A61B 5/0422
                                                600/407
(Continued)

FOREIGN PATENT DOCUMENTS

JP    2009-39429 A    2/2009
JP    2011-506033 A   3/2011

OTHER PUBLICATIONS

International Search Report dated Dec. 24, 2013 for PCT/JP2013/075374 filed on Sep. 19, 2013 with English Translation.
(Continued)

*Primary Examiner* — Abderrahim Merouan
(74) *Attorney, Agent, or Firm* — Oblon, McClelland, Maier & Neustadt, L.L.P.

(57) ABSTRACT

An image processing system according to an embodiment includes an input unit, an output unit, an acquiring unit, and a display unit. The input unit receives setting of a landmark in first medical image data obtained by capturing a certain tissue of a subject. The output unit outputs data including information of the position of the landmark in the first medical image data as output data. The acquiring unit receives the output data and acquires, based on one or a plurality of pieces of second medical image data obtained by capturing the certain tissue of the subject and the position of the landmark, three-dimensional position information of the landmark in a three-dimensional capturing space of the second medical image data. The display unit displays image data obtained by superimposing the first medical image data
(Continued)

on the second medical image data, based on the three-dimensional position information.

15 Claims, 21 Drawing Sheets

(51) Int. Cl.
<table>
<tr><td>A61B 8/08</td><td>(2006.01)</td></tr>
<tr><td>A61B 8/00</td><td>(2006.01)</td></tr>
<tr><td>A61B 6/00</td><td>(2006.01)</td></tr>
<tr><td>G06T 11/60</td><td>(2006.01)</td></tr>
<tr><td>G06T 7/70</td><td>(2017.01)</td></tr>
</table>

(52) U.S. Cl.
CPC ............ *A61B 6/503* (2013.01); *A61B 8/0883* (2013.01); *A61B 8/467* (2013.01); *A61B 8/5207* (2013.01); *A61B 8/5261* (2013.01); *G06T 7/70* (2017.01); *G06T 11/60* (2013.01); *G06T 2207/10116* (2013.01); *G06T 2207/10132* (2013.01); *G06T 2207/20221* (2013.01); *G06T 2207/30004* (2013.01); *G06T 2207/30048* (2013.01); *G06T 2219/2004* (2013.01)

(58) Field of Classification Search
CPC . G06T 2207/20221; G06T 2207/30004; G06T 2207/30; A61B 6/4417; A61B 6/4441; A61B 6/487; A61B 6/503; A61B 8/0883; A61B 8/467; A61B 8/5207; A61B 8/5261
See application file for complete search history.

(56) References Cited

U.S. PATENT DOCUMENTS

<table>
<tr><td>2008/0043901 A1*</td><td>2/2008</td><td>Maschke ............... G01T 1/1615<br>378/4</td></tr>
<tr><td>2008/0085042 A1*</td><td>4/2008</td><td>Trofimov ............... A61B 5/042<br>382/128</td></tr>
<tr><td>2008/0212858 A1*</td><td>9/2008</td><td>Boese ...................... G06T 7/38<br>382/130</td></tr>
<tr><td>2009/0043200 A1</td><td>2/2009</td><td>Abe</td></tr>
<tr><td>2010/0254583 A1</td><td>10/2010</td><td>Chan et al.</td></tr>
<tr><td>2013/0150703 A1*</td><td>6/2013</td><td>Buchalter ............ A61B 6/0492<br>600/411</td></tr>
</table>

OTHER PUBLICATIONS

International Written Opinion dated Dec. 24, 2013 for PCT/JP2013/075374 filed on Sep. 19, 2013.

* cited by examiner

FIG.3
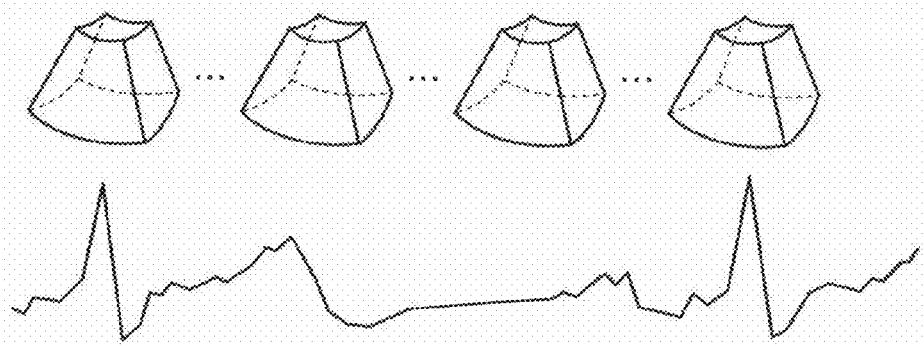
FIG.4
FIRST FRAME 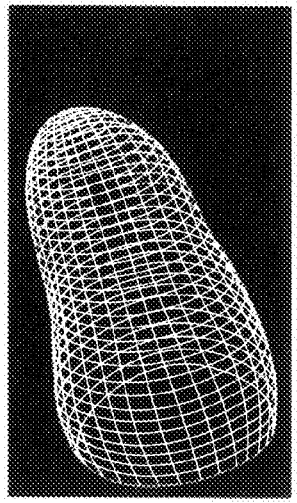      ............      n-TH FRAME 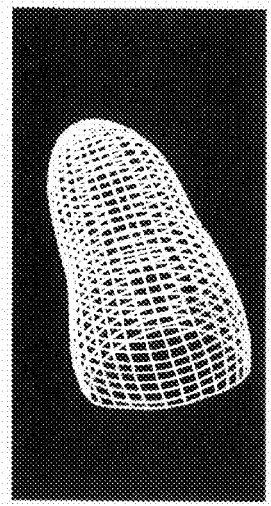

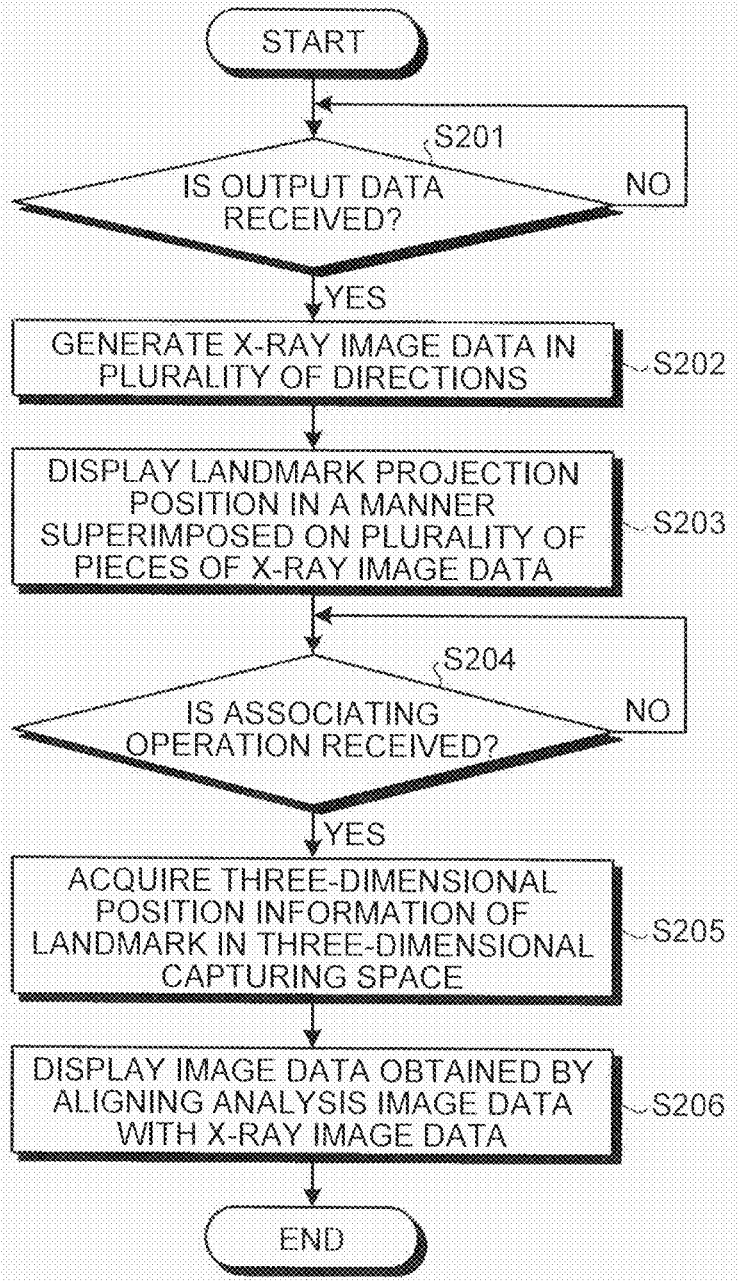

IMAGE PROCESSING SYSTEM, X-RAY DIAGNOSTIC APPARATUS, AND IMAGE PROCESSING METHOD

CROSS-REFERENCE TO RELATED APPLICATIONS

This application is a continuation of International Application No. PCT/JP2013/075374, filed on Sep. 19, 2013 which claims the benefit of priority of the prior Japanese Patent Application No. 2012-207492, filed on Sep. 20, 2012 and Japanese Patent Application No. 2013-194601, filed on Sep. 19, 2013, the entire contents of which are incorporated herein by reference.

FIELD

Embodiments described herein relate generally to an image processing system, an X-ray diagnostic apparatus, and an image processing method.

BACKGROUND

Conventionally, cardiac resynchronization therapy (CRT) is known as one of methods for treating heart failure. The CRT is a treatment method for correcting asynchrony in heart motion and restoring a pump function of the heart to nearly a normal state by placing an electrode (a pacing lead) of a pacemaker into an area at which delay in propagation of electric stimulation occurs in the heart (hereinafter, referred to as a delay area). In the CRT, a doctor places the electrode into a vein closest to the delay area while referring to an X-ray image fluoroscopically captured by an X-ray diagnostic apparatus.

Conventionally, delay areas are diagnosed using information of electrophysiology (EP), or by EP mapping in recent years, for example. In recent years, it has been known that delay areas can be diagnosed by a non-invasive analysis using an ultrasonic diagnostic apparatus. Specifically, a method for analyzing heart wall motion quantitatively by echocardiography has been in practical use in recent years. Such an analysis method can display an analysis image in which indices of local heart wall motion (e.g., strain) are mapped on an endomyocardium and between an endomyocardium and an epimyocardium in an ultrasound image in a color tone varying depending on the value. Because a heart is a tissue in which a myocardium is moved by mechanical excitation caused by electric stimulation, a delay area can be displayed as an area in which the heart wall motion is not synchronized (an asynchronous area) in the analysis image. The CRT treatment, however, is carried out under X-ray fluoroscopic guidance, and the analysis image is simply notified to the doctor as prior information to develop a treatment plan. Actually, it is not yet realized that the doctor is informed of a position into which the pacing lead is to be placed under the X-ray fluoroscopic guidance for the CRT treatment. On the other hand, there have been technologies for displaying an X-ray fluoroscopic image with another image superimposed thereon being developed. Since an endocardial surface and an epicardial surface of a heart wall are hard to distinguish, it is difficult to align an X-ray image with an analysis image, that is, an X-ray image with an ultrasound image.

BRIEF DESCRIPTION OF THE DRAWINGS

FIG. 3, FIG. 4, FIG. 5, FIG. 6 and FIG. 7 are views for explaining an analyzing unit according to the first embodiment;

FIG. 20 is a flowchart for explaining an example of processing performed by the X-ray diagnostic apparatus according to the first embodiment;

DETAILED DESCRIPTION

An image processing system according to an embodiment includes an input unit, an output unit, an acquiring unit and a display unit. The input unit receives setting of a landmark in first medical image data obtained by capturing a certain tissue of a subject. The output unit outputs data including information of a position of the landmark in the first medical image data as output data. The acquiring unit receives the output data and acquires, based on one or a plurality of pieces of second medical image data obtained by capturing the certain tissue of the subject in one or a plurality of capturing directions, the one or the plurality of pieces of second medical image data corresponding to the respective capturing directions and based on the position of the landmark read from the output data, three-dimensional position information of the landmark in a three-dimensional capturing space of the second medical image data. The display unit displays image data obtained by superimposing the first medical image data on the second medical image data of the certain tissue, based on the three-dimensional position information of the landmark.

Exemplary embodiments of an image processing system are described below in greater detail with reference to the accompanying drawings.

First Embodiment

The following describes an exemplary configuration of an image processing system according to a first embodiment.

Figure 1:
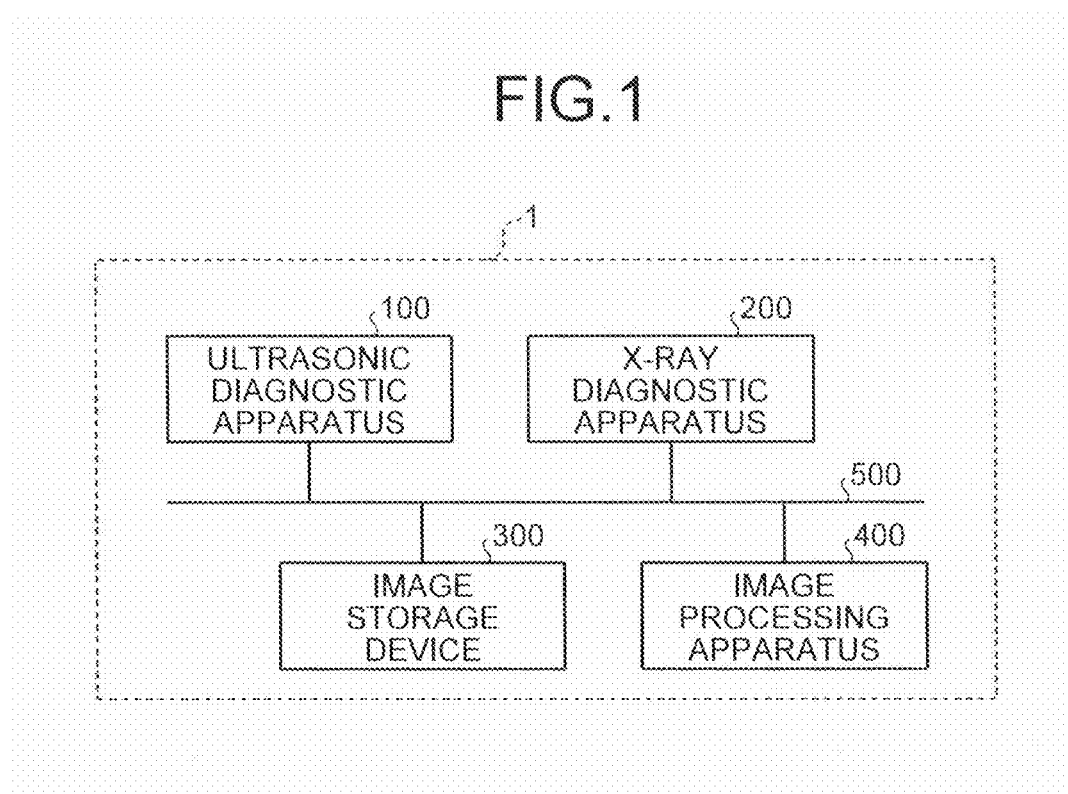
FIG. 1 is a diagram of an exemplary configuration of an image processing system according to a first embodiment.

FIG. 1 is a diagram of an exemplary configuration of the image processing system according to the first embodiment.

As illustrated in FIG. 1, the image processing system 1 according to the first embodiment includes an ultrasonic diagnostic apparatus 100, an X-ray diagnostic apparatus 200, an image storage device 300, and an image processing apparatus 400. The apparatuses illustrated in FIG. 1 are communicable with one another directly or indirectly via an in-hospital local area network (LAN) 500 installed in a hospital, for example. In the case where a picture archiving and communication system (PACS) is introduced into a medical image diagnostic system, for example, the apparatuses transmit and receive medical images and the like to and from one another in conformity to the digital imaging and communications in medicine (DICOM).

By transmitting and receiving data conforming to the DICOM, each of the apparatuses illustrated in FIG. 1 can read and display data received from the other apparatuses. In the present embodiment, any data conforming to an arbitrary standard may be transmitted and received as long as each of the apparatuses can process the data received from the other apparatuses.

An operator adjusts the position of an ultrasound probe that performs two-dimensional ultrasonic scanning, whereby the ultrasonic diagnostic apparatus 100 generates ultrasound image data on an arbitrary section. Furthermore, the ultrasonic diagnostic apparatus 100 performs three-dimensional ultrasonic scanning with a mechanical 4D probe or a 2D array probe, thereby generating three-dimensional ultrasound image data. The X-ray diagnostic apparatus 200 performs radiography with the position of a C-arm supporting an X-ray tube and an X-ray detector fixed, thereby generating two-dimensional X-ray image data. The ultrasonic diagnostic apparatus 100 and the X-ray diagnostic apparatus 200 according to the first embodiment will be described later in detail.

The image storage device 300 is a database that stores therein medical image data. Specifically, the image storage device 300 stores and retains medical image data transmitted from the ultrasonic diagnostic apparatus 100 and the X-ray diagnostic apparatus 200 in a storage unit of the image storage device 300. The medical image data stored in the image storage device 300 is stored in association with accompanying information, such as a patient ID, an examination ID, an apparatus ID, and a series ID.

The image processing apparatus 400 is a workstation and a personal computer (PC) used by doctors and laboratory technicians who work for a hospital to interpret a medical image, for example. An operator of the image processing apparatus 400 performs a search using a patient ID, an examination ID, an apparatus ID, a series ID, and other IDs, thereby acquiring necessary medical image data from the image storage device 300. Alternatively, the image processing apparatus 400 may receive image data directly from the ultrasonic diagnostic apparatus 100, and the X-ray diagnostic apparatus 200. Besides displaying a medical image for interpretation, the image processing apparatus 400 can perform various types of image processing on medical image data.

The following describes the case where the ultrasonic diagnostic apparatus 100 and the X-ray diagnostic apparatus 200 cooperate to perform an image processing method according to the present embodiment. A part or all of various types of processing performed by the ultrasonic diagnostic apparatus 100 and the X-ray diagnostic apparatus 200 may be performed by the image processing apparatus 400.

The image processing system 1 is not necessarily applied to the case where the PACS is introduced. The image processing system 1 is also applicable to the case where an electronic medical chart system that manages electronic medical charts accompanied with medical image data is introduced, for example. In such a case, the image storage device 300 is a database that stores therein the electronic medical charts. The image processing system 1 is also applicable to the case where a hospital information system (HIS) or a radiology information system (RIS) is introduced, for example.

Figure 2:
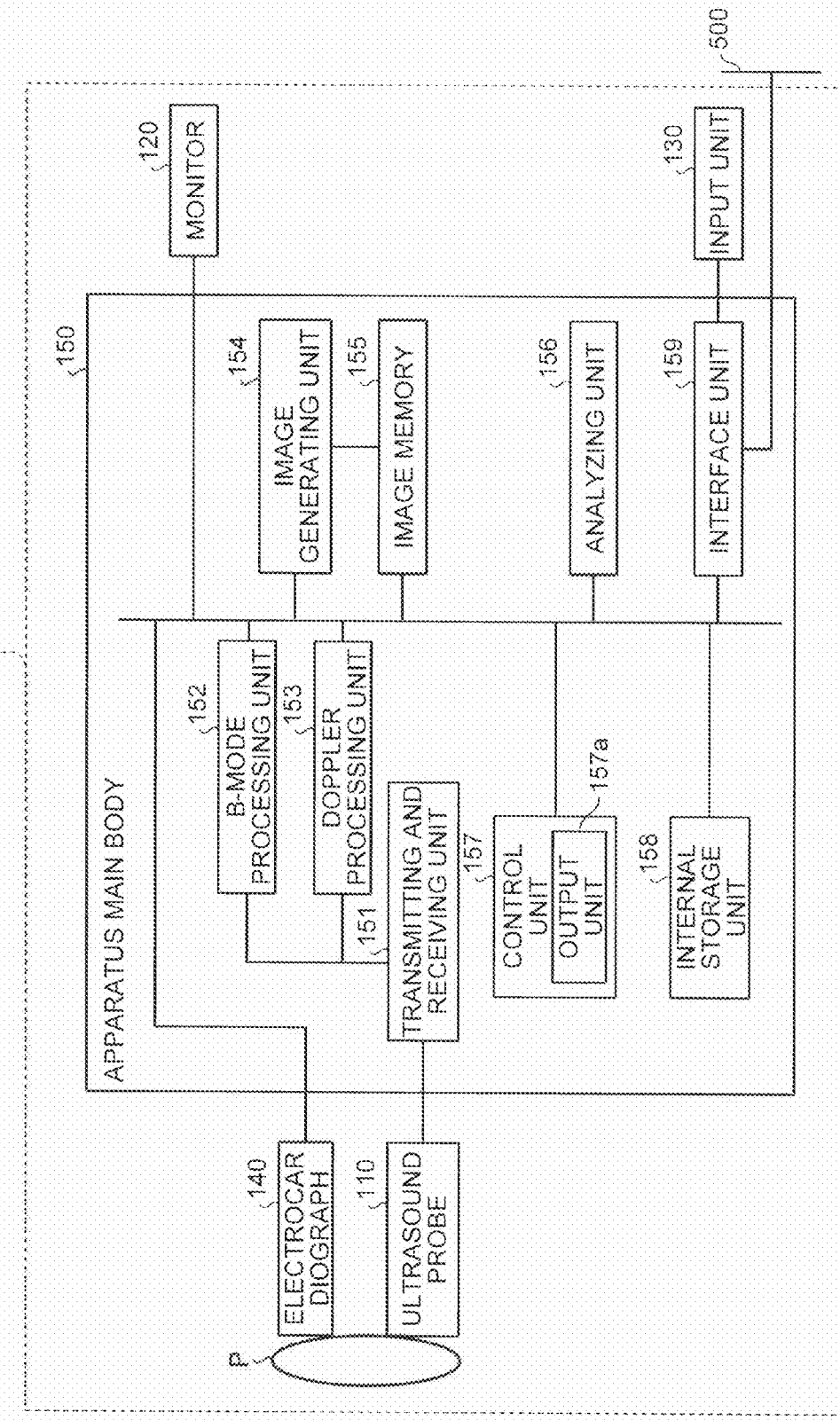
FIG. 2 is a block diagram of an exemplary configuration of an ultrasonic diagnostic apparatus according to the first embodiment.

The following describes an exemplary configuration of the ultrasonic diagnostic apparatus 100 illustrated in FIG. 1 with reference to FIG. 2. FIG. 2 is a block diagram of an exemplary configuration of the ultrasonic diagnostic apparatus according to the first embodiment. As illustrated in FIG. 1, the ultrasonic diagnostic apparatus 100 according to the first embodiment includes an ultrasound probe 110, a monitor 120, an input unit 130, an electrocardiograph 140, and an apparatus main body 150.

The ultrasound probe 110 transmits and receives ultrasonic waves. The ultrasound probe 110 includes a plurality of piezoelectric transducer elements, for example. The plurality of piezoelectric transducer elements generate ultrasonic waves based on a driving signal supplied from a transmitting and receiving unit 151 included in the apparatus main body 150, which will be described later. The ultrasound probe 110 receives reflected waves from a subject P and converts the reflected waves into an electrical signal. The ultrasound probe 110 further includes a matching layer provided to the piezoelectric transducer elements and a backing member that prevents ultrasonic waves from traveling rearward from the piezoelectric transducer elements, for example. The ultrasound probe 110 is connected to the apparatus main body 150 in an attachable and detachable manner.

If ultrasonic waves are transmitted from the ultrasound probe 110 to the subject P, the ultrasonic waves thus transmitted are sequentially reflected at an acoustic impedance discontinuous surface in a body tissue of the subject P. The ultrasonic waves are received by the plurality of piezoelectric transduce elements included in the ultrasound probe 110 as a reflected wave signal. The amplitude of the reflected wave signal thus received depends on difference in the acoustic impedance on the discontinuous surface on which the ultrasonic waves are reflected. A reflected wave signal obtained when the ultrasonic pulse thus transmitted is reflected by a moving bloodstream, the surface of a heart wall, or the like depends on a velocity component of the moving object with respect to an ultrasonic-wave transmitting direction because of the Doppler effect, thereby undergoing frequency shift.

The ultrasound probe 110 according to the first embodiment is an ultrasound probe that can scan the subject P two-dimensionally and scan the subject P three-dimensionally with ultrasonic waves. Specifically, the ultrasound probe 110 according to the first embodiment is a mechanical 4D probe that scans the subject P two-dimensionally using the plurality of piezoelectric transduce elements arranged in a line and scans the subject P three-dimensionally by oscillating the plurality of piezoelectric transduce elements at a predetermined angle (an oscillation angle). Alternatively, the ultrasound probe 110 according to the first embodiment is a 2D array probe that can perform ultrasonic scanning on the subject P three-dimensionally with the plurality of piezoelectric transduce elements arranged in a matrix. The 2D array probe can also scan the subject P two-dimensionally by focusing and transmitting the ultrasonic waves.

The input unit 130 includes a mouse, a keyboard, a button, a panel switch, a touch command screen, a foot switch, a trackball, and a joystick, for example. The input unit 130 receives various types of setting requests from an operator of the ultrasonic diagnostic apparatus 100 and transfers the various types of setting requests thus received to the apparatus main body 150. The setting information received from the operator by the input unit 130 according to the first embodiment will be described later in detail.

The monitor 120 displays a graphical user interface (GUI) through which the operator of the ultrasonic diagnostic apparatus inputs various types of setting request with the input unit 130 and displays ultrasound image data generated in the apparatus main body 150, for example.

The electrocardiograph 140 acquires an electrocardiogram (ECG) of the subject P as a biomedical signal of the subject P. The electrocardiograph 140 transmits the ECG thus acquired to the apparatus main body 150.

The apparatus main body 150 is a device that generates ultrasound image data based on a reflected wave signal received by the ultrasound probe 110. The apparatus main body 150 illustrated in FIG. 2 is a device that can generate two-dimensional ultrasound image data based on two-dimensional reflected wave data received by the ultrasound probe 110. Furthermore, the apparatus main body 150 illustrated in FIG. 2 is a device that can generate three-dimensional ultrasound image data based on three-dimensional reflected wave data received by the ultrasound probe 110.

As illustrated in FIG. 2, the apparatus main body 150 includes the transmitting and receiving unit 151, a B-mode processing unit 152, a Doppler processing unit 153, an image generating unit 154, an image memory 155, an analyzing unit 156, a control unit 157, an internal storage unit 158, and an interface unit 159.

The transmitting and receiving unit 151 includes a pulse generator, a transmission delay unit, a pulser, and other components, and supplies a driving signal to the ultrasound probe 110. The pulse generator repeatedly generates a rate pulse that forms transmission ultrasonic waves at a predetermined rate frequency. The transmission delay unit supplies delay times required for the respective piezoelectric transducer elements to focus ultrasonic waves generated from the ultrasound probe 110 into a beam and to determine the transmission directivity to the respective rate pulses generated by the pulse generator. The pulser applies a driving signal (a driving pulse) to the ultrasound probe 110 at a timing based on the rate pulse. Specifically, the transmission delay unit changes the delay times supplied to the respective rate pulses, thereby arbitrarily controlling the direction of transmission of the ultrasonic waves transmitted from the piezoelectric transducer element surface.

The transmitting and receiving unit 151 has a function to instantaneously change a transmission frequency, a transmission driving voltage, and other elements so as to perform a predetermined scanning sequence based on an instruction issued from the control unit 157, which will be described later. Specifically, the transmission driving voltage is changed by a linear-amplifier oscillating circuit that can instantaneously change the value of the transmission driving voltage or a mechanism that electrically switches a plurality of power-supply units.

The transmitting and receiving unit 151 further includes a pre-amplifier, an analog/digital (A/D) converter, a reception delay unit, and an adder, for example. The transmitting and receiving unit 151 performs various types of processing on a reflected wave signal received by the ultrasound probe 110, thereby generating reflected wave data. The pre-amplifier amplifies a reflected wave signal on each channel. The A/D converter performs A/D conversion on the reflected wave signal thus amplified. The reception delay unit supplies a delay time required to determine the reception directivity. The adder performs addition on the reflected wave signal processed by the reception delay unit, thereby generating reflected wave data. The addition performed by the adder emphasizes a reflection component in a direction corresponding to the reception directivity of the reflected wave signal. Based on the reception directivity and the transmission directivity, a synthetic beam for transmitting and receiving ultrasonic waves is formed.

To scan the subject P two-dimensionally, the transmitting and receiving unit 151 causes the ultrasound probe 110 to transmit a two-dimensional ultrasonic beam. The transmitting and receiving unit 151 generates two-dimensional reflected wave data from a two-dimensional reflected wave signal received by the ultrasound probe 110. To scan the subject P three-dimensionally, the transmitting and receiving unit 151 causes the ultrasound probe 110 to transmit a three-dimensional ultrasonic beam. The transmitting and receiving unit 151 generates three-dimensional reflected wave data from a three-dimensional reflected wave signal received by the ultrasound probe 110.

An output signal from the transmitting and receiving unit 151 may have various forms, including a signal containing phase information, which is called a radio frequency (RF) signal, and amplitude information obtained after envelope detection is performed, for example.

The B-mode processing unit 152 receives reflected wave data from the transmitting and receiving unit 151. The B-mode processing unit 152 performs logarithmic amplification, envelope detection, and other processing on the reflected wave data, thereby generating data (B-mode data) representing the signal intensity by the intensity of brightness.

The Doppler processing unit 153 performs a frequency analysis on velocity information in the reflected wave data received from the transmitting and receiving unit 151. The Doppler processing unit 153 extracts a bloodstream, a tissue, and a contrast medium echo component by the Doppler effect and generates data (Doppler data) by extracting moving object information, such as velocity, dispersion, and power, at multiple points.

The B-mode processing unit 152 and the Doppler processing unit 153 according to the first embodiment can process both two-dimensional reflected wave data and three-dimensional reflected wave data. In other words, the B-mode processing unit 152 generates two-dimensional B-mode data from two-dimensional reflected wave data and generates three-dimensional B-mode data from three-dimensional reflected wave data. The Doppler processing unit 153 generates two-dimensional Doppler data from two-dimensional reflected wave data and generates three-dimensional Doppler data from three-dimensional reflected wave data.

The image generating unit 154 generates ultrasound image data from the data generated by the B-mode processing unit 152 and the Doppler processing unit 153. In other words, the image generating unit 154 generates two-dimensional B-mode image data representing the intensity of reflected waves by the brightness from the two-dimensional B-mode data generated by the B-mode processing unit 152. Furthermore, the image generating unit 154 generates two-dimensional Doppler image data indicating the moving object information from the two-dimensional Doppler data generated by the Doppler processing unit 153. The two-dimensional Doppler image data is a velocity image, a dispersion image, a power image, or a combination image of these images.

Typically, the image generating unit 154 converts (scan-converts) a scanning-line signal row in ultrasonic scanning into a scanning-line signal row in a video format as exemplified by television and the like, thereby generating ultrasound image data for display. Specifically, the image generating unit 154 performs coordinate transformation based on the form of the ultrasonic scanning performed by the ultrasound probe 110, thereby generating the ultrasound image data for display. The image generating unit 154 performs various types of image processing besides the scan-conversion on a plurality of image frames thus scan-converted. Examples of the various types of image processing include image processing for regenerating a brightness average value image (smoothing processing) and image processing using a differential filter in an image (edge emphasizing processing). The image generating unit 154 synthesizes character information of various types of parameters, a scale, and a body mark on the ultrasound image data, for example.

In other words, the B-mode data and the Doppler data are ultrasound image data before the scan-conversion. The data generated by the image generating unit 154 is ultrasound image data for display after the scan-conversion. The B-mode data and the Doppler data are also referred to as raw data.

The image generating unit 154 performs coordinate transformation on the three-dimensional B-mode data generated by the B-mode processing unit 152, thereby generating three-dimensional B-mode image data. Furthermore, the image generating unit 154 performs coordinate transformation on the three-dimensional Doppler data generated by the Doppler processing unit 153, thereby generating three-dimensional Doppler image data. In other words, the image generating unit 154 generates "three-dimensional B-mode image data and three-dimensional Doppler image data" as "three-dimensional ultrasound image data".

To generate various types of two-dimensional image data for displaying three-dimensional ultrasound image data (volume data) on the monitor 120, the image generating unit 154 performs rendering on the volume data. Examples of the rendering performed by the image generating unit 154 include processing for generating multi-planer reconstruction (MPR) image data from volume data by performing MPR. Examples of the rendering performed by the image generating unit 154 further include processing for performing "curved MPR" on volume data and processing for performing "maximum intensity projection" on volume data. Examples of the rendering performed by the image generating unit 154 further include volume rendering (VR) for generating two-dimensional image data reflecting three-dimensional information.

The image memory 155 is a memory that stores therein image data for display generated by the image generating unit 154. The image memory 155 can also store therein data generated by the B-mode processing unit 152 and the Doppler processing unit 153. The B-mode data and the Doppler data stored in the image memory 155 can be retrieved by the operator after a diagnosis, for example, and are converted into ultrasound image data for display via the image generating unit 154. The image generating unit 154 stores ultrasound image data and a time of ultrasonic scanning performed to generate the ultrasound image data in the image memory 155 in association with an electrocardiogram (ECG) transmitted from the electrocardiograph 140. The analyzing unit 156 and the control unit 157, which will be described later, refer to the data stored in the image memory 155, thereby acquiring a cardiac time phase in the ultrasonic scanning performed to generate the ultrasound image data.

The internal storage unit 158 stores therein various types of data, such as a control program for performing transmission and reception of ultrasonic waves, image processing, and display processing, diagnosis information (e.g., a patient ID and findings of a doctor), a diagnosis protocol, and various types of body marks. Furthermore, the internal storage unit 158 is used to retain image data stored in the image memory 155 as needed, for example. The data stored in the internal storage unit 158 can be transferred to external apparatuses via the interface unit 159, which will be described later. The external apparatuses correspond to the X-ray diagnostic apparatus 200, the image storage device 300, and the image processing apparatus 400 illustrated in FIG. 1, for example.

The analyzing unit 156 is provided to the apparatus main body 150 to perform a computer-aided diagnosis (CAD). The analyzing unit 156 acquires ultrasound image data stored in the image memory 155 and performs an image analysis thereon. The analyzing unit 156 stores the analysis result in the image memory 155 and the internal storage unit 158.

Specifically, the analyzing unit 156 analyzes an ultrasound image data group in a time series generated by performing ultrasonic scanning on the subject P to generate analysis image data relating to local motion in the certain tissue. In the first embodiment, the analyzing unit 156 analyzes a three-dimensional ultrasound image data group in a time series to generate three-dimensional analysis image data, the three-dimensional ultrasound image data group being generated by performing three-dimensional ultrasonic scanning on the subject.

The certain tissue corresponds to a heart, and the analyzing unit 156 generates information relating to motion in each region of the heart wall. The analyzing unit 156 generates analysis image data in which heart wall motion information is mapped on the endomyocardium and between the endomyocardium and the epimyocardium in the ultrasound image data. The analyzing unit 156 according to the first embodiment uses the three-dimensional ultrasound image data group, thereby generating three-dimensional heart wall motion information.

The following describes the analysis performed by the analyzing unit 156 according to the first embodiment with reference to FIG. 3 to FIG. 7. FIG. 3 to FIG. 7 are views for explaining the analyzing unit according to the first embodiment.

In the first embodiment, the operator uses the ultrasound probe 110 that can perform three-dimensional scanning, thereby performing three-dimensional scanning on the left side of the heart of the subject P by apical approach for a time period equal to or longer than one heartbeat, for example. As a result, the image generating unit 154 generates a plurality of pieces of time-series three-dimensional ultrasound image data in a time period equal to or longer than one heartbeat and stores the plurality of pieces of three-dimensional ultrasound image data in the image memory 155. The plurality of pieces of three-dimensional ultrasound image data stored in the image memory 155 are a three-dimensional ultrasound image data group generated by performing ultrasonic scanning on the heart including at least the left ventricle for a time period equal to or longer than one heartbeat. The three-dimensional ultrasound image data group is a three-dimensional B-mode image data group.

As illustrated in FIG. 3, the analyzing unit 156 acquires the plurality of pieces of time-series three-dimensional ultrasound image data in a time period equal to or longer than one heartbeat. Each of the plurality of pieces of three-dimensional ultrasound image data includes the left ventricle of the subject P. The analyzing unit 156 derives time-series data of the heart wall motion information in the left ventricle from the three-dimensional ultrasound image data group. Specifically, the analyzing unit 156 uses the result of tracking of a tracking point, which will be described later, performed by processing including pattern matching between a plurality of pieces of image data, thereby deriving the heart wall motion information.

More specifically, the analyzing unit 156 uses the result of 3D speckle tracking (hereinafter, referred to as "3DT") performed on three-dimensional moving image data obtained by a three-dimensional echocardiography method, thereby deriving the heart wall motion information. The speckle tracking method is a method for estimating motion accurately by performing the pattern matching in combination with an optical flow method and various types of spatiotemporal interpolation, for example. Some speckle tracking methods estimate the motion without performing the pattern matching.

The input unit 130, for example, receives a display request of the first frame (first volume) of the three-dimensional ultrasound image data group from the operator. The control unit 157 to which the display request is transferred reads three-dimensional ultrasound image data of the first frame from the image memory 155 and displays the three-dimensional ultrasound image data on the monitor 120. The control unit 157, for example, causes the image generating unit 154 to generate a plurality of pieces of MPR image data by cutting the three-dimensional ultrasound image data of the first frame on sections in a plurality of directions and displays the plurality of pieces of MPR image data on the monitor 120.

The operator refers to the plurality of pieces of MPR image data displayed on the monitor 120, thereby setting a plurality of tracking points used for performing 3DT. The operator, for example, traces the positions of the endocardium of the left ventricle and the epimyocardium in each piece of MPR image data, thereby specifying the endocardial outline and the epicardial outline. The analyzing unit 156 forms a three-dimensional endocardial outline and a three-dimensional epicardial outline from the endocardial outline and the epicardial outline thus specified. The analyzing unit 156 sets the points forming the three-dimensional endocardial outline in the first frame as tracking points as illustrated in FIG. 4. The analyzing unit 156 also sets the points forming the three-dimensional epicardial outline in the first frame as tracking points, which is not illustrated. The analyzing unit 156 sets template data to each of the plurality of tracking points set in the first frame. The template data is formed of a plurality of voxels with the tracking points being the center.

The analyzing unit 156 searches for an area that best matches to the speckle pattern of the template data between two frames, thereby tracking the template data to find out to which position the template data moves in the next frame. Thus, the analyzing unit 156 tracks each tracking points in the first frame to find out to which positions in the n-th frame each of the tracking points in the first frame moves as illustrated in FIG. 4. The mesh used for setting the tracking points may be set by the analyzing unit 156 detecting the endocardial surface and the epicardial surface of the left ventricle included in the first frame.

The analyzing unit 156 performs 3DT on the three-dimensional ultrasound image data group for the entire left ventricle (e.g., the endocardium of the left ventricle and the epicardium of the left ventricle). Based on the result of the 3DT performed on the three-dimensional ultrasound image data group, the analyzing unit 156 generates time-series data of the heart wall motion information on each tracking point. The analyzing unit 156 derives strain as the heart wall motion information from the result of the 3DT of the endocardium and the epicardium, for example. The analyzing unit 156 derives strain in the longitudinal direction (LS), strain in the circumferential direction (CS), and strain in the radial direction (RS).

Alternatively, the analyzing unit 156 derives the area change ratio (AC) of the endocardial surface of the left ventricle as the heart wall motion information from the result of the 3DT of the endocardium, for example. Still alternatively, the analyzing unit 156 may derive displacement from the result of the 3DT of the endocardium or the epicardium, for example. In the case where the displacement is employed as the heart wall motion information, the analyzing unit 156 can derive displacement in the longitudinal direction (LD) and displacement in the radial direction (RD). Alternatively, the analyzing unit 156 may derive absolute displacement (AD) of the tracking points at a time phase other than a reference phase with respect to the positions of the respective tracking points at a reference time phase (e.g., an R-wave). Still alternatively, to grasp the asynchrony in the motion of the heart, the analyzing unit 156 may derive an analysis result of mapping of time when the strain value is equal to or larger than a certain value or an analysis result of mapping of time when the strain value reaches the maximum.

The analyzing unit 156 may generate the time-series data of the heart wall motion information for each tracking point or for each local region. The analyzing unit 156 derives local heart wall motion information using a segmented region of 16 or 17 segments, which is recommended by the American Society of Echocardiography (ASE) and the American Heart Association (AHA), for example. Examples of the segments recommended by the ASE include an anterior wall septum (ant-sept.), an anterior wall (ant.), a lateral wall (lat.), a posterior wall (post.), an inferior wall (inf.), and a septum (sept.)

Figure 5:
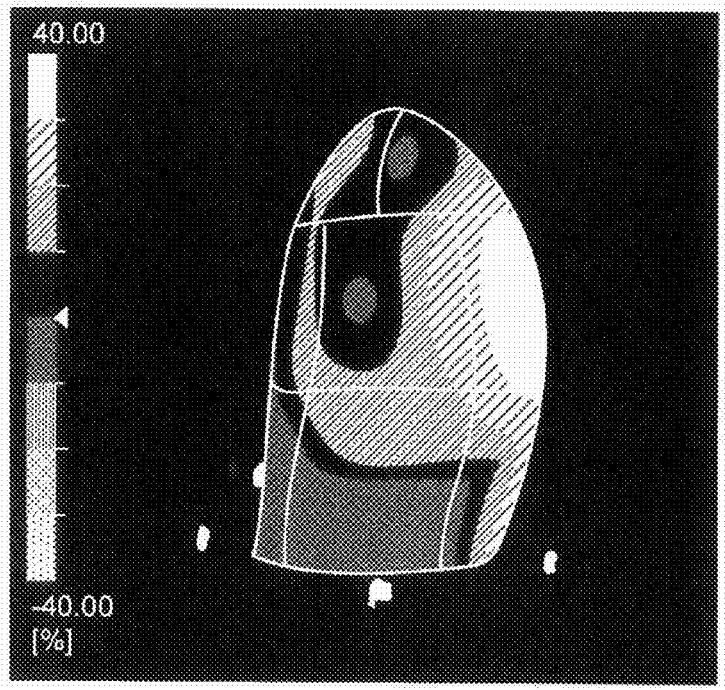

The analyzing unit 156 converts the values of the heart wall motion information obtained at the respective tracking points into color scales and maps the values onto a surface rendering image of the three-dimensional endocardial outline, thereby generating three-dimensional analysis image data as illustrated in FIG. 5, for example. The operator can observe the three-dimensional analysis image data illustrated in FIG. 5 on the monitor 120 in various directions by moving the viewpoint position. Alternatively, the analyzing unit 156 converts the values of the heart wall motion information obtained at the respective tracking points into color scales and maps the values onto a polar-map of 16 segments, thereby generating three-dimensional analysis image data as illustrated in FIG. 6, for example.

Figure 6:
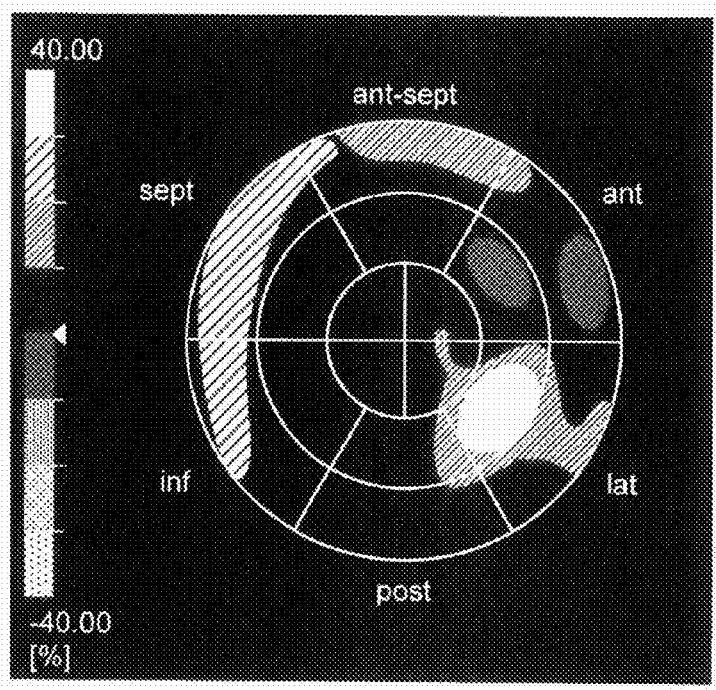

FIG. 5 and FIG. 6 illustrate the case where the AC is employed as the heart wall motion information. The three-dimensional analysis image data illustrated in FIG. 5 and FIG. 6 are three-dimensional analysis image data at a specific time phase. The analyzing unit 156 generates three-dimensional analysis image data at each time phase. In other words, the analyzing unit 156 generates a time-series three-dimensional distribution image data group.

Alternatively, the analyzing unit 156 converts the values of the heart motion information obtained at the respective tracking points into color scales and maps the values between the endocardial surface and the epicardial surface in three-dimensional ultrasound image data, thereby generating three-dimensional analysis image data, for example. The display format illustrated in FIG. 7 is an example of the display format of the three-dimensional analysis image data.

The image generating unit 154, for example, generates a plurality of pieces of MPR image data from the three-dimensional analysis image data. In the example illustrated in FIG. 7, the image generating unit 154 generates MPR image data in a cardiac apex four-chamber view from three-dimensional analysis image data of 16 segments as image data displayed in an area A. In the example illustrated in FIG. 7, the image generating unit 154 generates MPR image data in a cardiac apex two-chamber view from the three-dimensional analysis image data as image data displayed in an area B.

Figure 7:

In the example of FIG. 7, the image generating unit 154 generates MPR image data in a short-axis view at a level close to the cardiac apex from the three-dimensional analysis image data as image data displayed in an area C3. In the example of FIG. 7, the image generating unit 154 generates MPR image data in a short-axis view at a level close to the cardiac base from the three-dimensional analysis image data as image data displayed in an area C7. In the example of FIG. 7, the image generating unit 154 generates MPR image data in a short-axis view at a level intermediate between the cardiac apex and the cardiac base from the three-dimensional analysis image data as image data displayed in an area C5.

Referring back to FIG. 2, the control unit 157 controls the entire processing of the ultrasonic diagnostic apparatus 100. Specifically, the control unit 157 controls the processing of the transmitting and receiving unit 151, the B-mode processing unit 152, the Doppler processing unit 153, the image generating unit 154, and the analyzing unit 156 based on various types of setting requests received from the operator via the input unit 130 and various types of control programs and various types of data read from the internal storage unit 158. The control unit 157 performs control such that the monitor 120 displays ultrasound image data for display stored in the image memory 155 and the internal storage unit 158. Furthermore, the control unit 157 performs control such that the monitor 120 displays the processing result of the analyzing unit 156.

The control unit 157 outputs the processing result of the analyzing unit 156 and setting information received from the operator by the input unit 130 to the external apparatuses via the interface unit 159, which will be described later. The external apparatuses correspond to the X-ray diagnostic apparatus 200, the image storage device 300, and the image processing apparatus 400 illustrated in FIG. 1, for example. The control unit 157 according to the first embodiment includes an output unit 157a illustrated in FIG. 2 serving as a processing unit that outputs output data and controls the data format of the output data. The processing performed by the output unit 157a will be described later in detail.

The interface unit 159 is an interface provided for the input unit 130, an in-hospital LAN 500, the X-ray diagnostic apparatus 200, the image storage device 300, and the image processing apparatus 400. Various types of setting information and various types of instructions received from the operator by the input unit 130 are transferred to the control unit 157 by the interface unit 159, for example. Output data output from the output unit 157a is transmitted to the X-ray diagnostic apparatus 200 by the interface unit 159 via the in-hospital LAN 500, for example.

Figure 8:
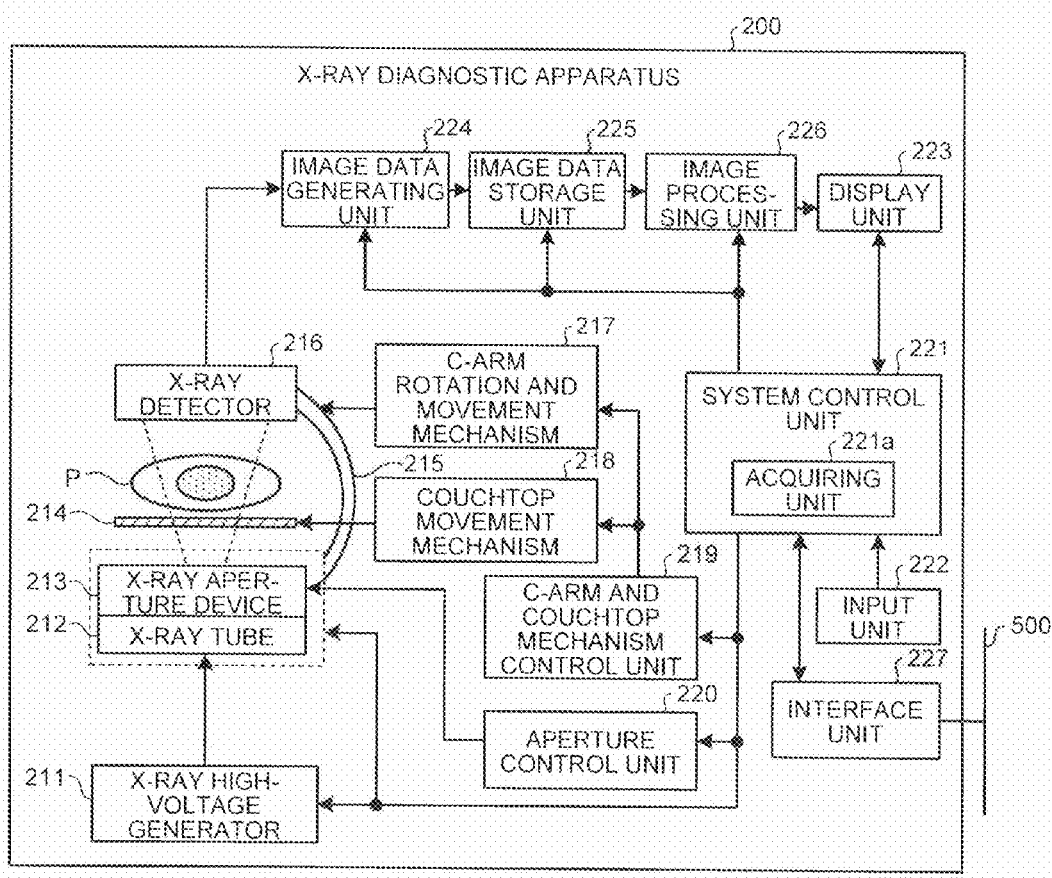
FIG. 8 is a block diagram of an exemplary configuration of an X-ray diagnostic apparatus according to the first embodiment.

The following describes an exemplary configuration of the X-ray diagnostic apparatus 200 illustrated in FIG. 1 with reference to FIG. 8. FIG. 8 is a block diagram of an exemplary configuration of the X-ray diagnostic apparatus according to the first embodiment. As illustrated in FIG. 8, the X-ray diagnostic apparatus 200 according to the first embodiment includes an X-ray high-voltage generator 211, an X-ray tube 212, an X-ray aperture device 213, a couchtop 214, a C-arm 215, and an X-ray detector 216. The X-ray diagnostic apparatus 200 according to the first embodiment further includes a C-arm rotation and movement mechanism 217, a couchtop movement mechanism 218, a C-arm and couchtop mechanism control unit 219, an aperture control unit 220, a system control unit 221, an input unit 222, and a display unit 223. The X-ray diagnostic apparatus 200 according to the first embodiment further includes an image data generating unit 224, an image data storage unit 225, and an image processing unit 226.

The X-ray high-voltage generator 211 generates a high voltage and supplies the high voltage thus generated to the X-ray tube 212 based on the control of the system control unit 221. The X-ray tube 212 uses the high voltage supplied from the X-ray high-voltage generator 211, thereby generating an X-ray.

The X-ray aperture device 213 limits the X-ray generated by the X-ray tube 212 such that a region of interest of the subject P is selectively irradiated with the X-ray based on the control of the aperture control unit 220. The X-ray aperture device 213 includes four slidable aperture blades, for example. Based on the control of the aperture control unit 220, the X-ray aperture device 213 slides the aperture blades to limit the X-ray generated by the X-ray tube 212, thereby irradiating the subject P with the X-ray. The couchtop 214 is a bed on which the subject P is placed and is arranged on a couch, which is not illustrated.

The X-ray detector 216 detects an X-ray transmitting through the subject P. The X-ray detector 216 includes detection elements arrayed in a matrix, for example. The detection elements each convert the X-ray transmitting through the subject P into an electrical signal, accumulate the electrical signal, and transmit the electrical signal thus accumulated to the image data generating unit 224.

The C-arm 215 holds the X-ray tube 212, the X-ray aperture device 213, and the X-ray detector 216. The X-ray tube 212 and the X-ray aperture device 213 are arranged in a manner facing the X-ray detector 216 with the subject P interposed therebetween by the C-arm 215.

The C-arm rotation and movement mechanism 217 is a mechanism that rotates and moves the C-arm 215. The couchtop movement mechanism 218 is a mechanism that moves the couchtop 214. The C-arm and couchtop mechanism control unit 219 controls the C-arm rotation and movement mechanism 217 and the couchtop movement mechanism 218 based on the control of the system control unit 221, thereby adjusting rotation and movement of the C-arm 215 and movement of the couchtop 214. The aperture control unit 220 adjusts the degree of opening of the aperture blades included in the X-ray aperture device 213 based on the control of the system control unit 221, thereby controlling the irradiation range of the X-ray with which the subject P is irradiated.

The image data generating unit 224 uses the electrical signal converted from the X-ray by the X-ray detector 216, thereby generating X-ray image data. The image data generating unit 224 then stores the X-ray image data thus generated in the image data storage unit 225. The image data generating unit 224, for example, performs current/voltage conversion, analog/digital (A/D) conversion, and parallel/serial conversion on the electrical signal received from the X-ray detector 216, thereby generating X-ray image data.

The image data storage unit 225 stores therein image data generated by the image data generating unit 224. The image processing unit 226 performs various types of image processing on the image data stored in the image data storage unit 225. The image processing performed by the image processing unit 226 will be described later in detail.

The input unit 222 receives various types of instructions issued from an operator, such as a doctor and a technician, who operates the X-ray diagnostic apparatus 200. The input unit 222 includes a mouse, a keyboard, a button, a trackball, and a joystick, for example. The input unit 222 transfers the instructions received from the operator to the system control unit 221.

The display unit 223 displays a GUI that receives an instruction from the operator and the image data stored in the image data storage unit 225, for example. The display unit 223 includes a monitor, for example. The display unit 223 may include a plurality of monitors.

The system control unit 221 controls the entire operation of the X-ray diagnostic apparatus 200. The system control unit 221, for example, controls the X-ray high-voltage generator 211 based on an instruction from the operator transferred from the input unit 222, thereby adjusting the voltage supplied to the X-ray tube 212. Thus, the system control unit 221 controls the amount of the X-ray with which the subject P is irradiated and ON/OFF of irradiation of the X-ray. The system control unit 221, for example, controls the C-arm and couchtop mechanism control unit 219 based on an instruction from the operator, thereby adjusting rotation and movement of the C-arm 215 and movement of the couchtop 214. The system control unit 221, for example, controls the aperture control unit 220 based on an instruction from the operator, thereby adjusting the degree of opening of the aperture blades included in the X-ray aperture device 213. Thus, the system control unit 221 controls the irradiation range of the X-ray with which the subject P is irradiated.

The system control unit 221 controls the image data generation processing performed by the image data generating unit 224, the image processing performed by the image processing unit 226, and other processing based on an instruction from the operator. The system control unit 221 performs control such that the monitor of the display unit 223 displays the GUI that receives an instruction from the operator and displays the image data stored in the image data storage unit 225, for example.

To perform the various types of processing using output data received from the ultrasonic diagnostic apparatus 100, the system control unit 221 includes an acquiring unit 221a as illustrated in FIG. 8. The processing performed by the acquiring unit 221a will be described later in detail.

The interface unit 227 is an interface provided for the in-hospital LAN 500, the ultrasonic diagnostic apparatus 100, the image storage device 300, and the image processing apparatus 400. The interface unit 227 according to the present embodiment, for example, receives output data output from the ultrasonic diagnostic apparatus 100 and transfers the output data thus received to the acquiring unit 221a included in the system control unit 221.

The explanation has been made of the entire configuration of the image processing system 1 according to the first embodiment. With this configuration, the image processing system 1 according to the first embodiment specifies an area requiring treatment by ultrasonography using the ultrasonic diagnostic apparatus 100. Specifically, an asynchronous area into which an electrode of a pacemaker is to be placed is specified from the analysis image data generated by the analyzing unit 156 in cardiac resynchronization therapy (CRT). In the CRT, the doctor places the electrode into a vein closest to the asynchronous area while refereeing to an X-ray image fluoroscopically captured by the X-ray diagnostic apparatus 200. Because the endocardial surface and the epicardial surface of the heart wall are hard to distinguish under X-ray fluoroscopic guidance, it is difficult to align X-ray image data with analysis image data, that is, X-ray image data with ultrasound image data.

Figure 9:
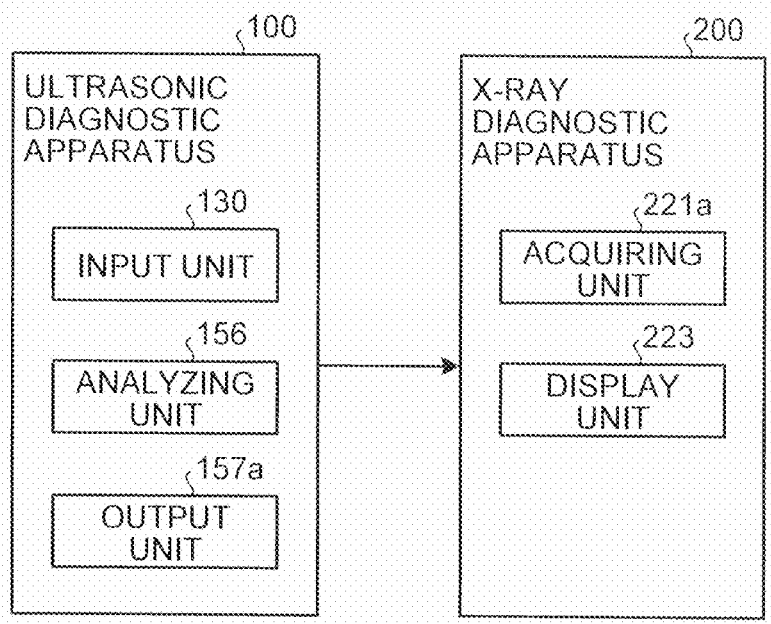
FIG. 9 is a diagram of processing units that carry out an image processing method performed by the image processing system according to the first embodiment.

To identify an area specified in the ultrasonic diagnosis under X-ray fluoroscopic guidance, the units illustrated in FIG. 9 perform the following processing in the first embodiment. FIG. 9 is a diagram of processing units that carry out an image processing method performed by the image processing system according to the first embodiment.

In the first embodiment, the input unit 130 included in the ultrasonic diagnostic apparatus 100 receives setting of a landmark in first medical image data obtained by capturing a certain tissue of a subject P. Specifically, the input unit 130 receives, in the first medical image data, setting of the landmark at a position corresponding to the specific tissue identifiable in second medical image data. The first medical image data is medical image data in which the heart serving as the certain tissue is depicted and in which motion of the heart (the certain tissue) is analyzable. Specifically, the first medical image data is ultrasound image data in which the motion of the heart is analyzable and the certain tissue (heart) of the subject P is depicted.

The second medical image data is medical image data visualizing a specific tissue. Specifically, the second medical image data is medical image data obtained by performing contrast enhanced radiography on the certain tissue and is X-ray image data obtained by performing contrast enhanced radiography. Alternatively, the second medical image data is medical image data obtained by capturing the specific tissue into which an instrument is inserted and is X-ray image data obtained by performing non-contrast radiography. The instrument described above is a guide wire inserted into the specific tissue. Because the guide wire is radiopaque, X-ray image data captured when the guide wire is inserted depicts a region corresponding to the specific tissue clearly without injecting a contrast medium.

In the first embodiment, for example, the input unit 130 receives setting of the landmark at a position, in the ultrasound image data depicting the certain tissue (heart) of the subject P, corresponding to the specific tissue identifiable in X-ray image data.

The output unit 157a included in the ultrasonic diagnostic apparatus 100 outputs data including information of a position of the landmark in the first medical image data as output data. In the first embodiment, the output unit 157a outputs data including the information of the position of the landmark in the ultrasound image data as output data. The output unit 157a, for example, outputs data obtained by adding the information of the position of the landmark to the three-dimensional analysis image data generated by the analyzing unit 156 as output data.

The acquiring unit 221a included in the X-ray diagnostic apparatus 200 receives the output data and acquires, based on one or a plurality of pieces of second medical image data obtained by capturing the certain tissue of the subject P in one or a plurality of capturing directions, the one or the plurality of pieces of second medical image data corresponding to the respective capturing directions and based on the position of the landmark read from the output data. Alternatively, the acquiring unit 221a receives the output data and acquires three-dimensional position information of the landmark in a three-dimensional capturing space of a piece of second medical image data based on the piece of second medical image data obtained by capturing the certain tissue of the subject P in a capturing direction and corresponding to the capturing direction and on the position of the landmark read from the output data. The three-dimensional capturing space is a three-dimensional capturing space of the X-ray diagnostic apparatus 200. "A plurality of pieces of X-ray image data" obtained by performing radiography in a plurality of capturing directions in the three-dimensional capturing space of the X-ray diagnostic apparatus 200 serves as the "plurality of pieces of second medical image data". "A piece of X-ray image data" obtained by performing radiography in a capturing direction in the three-dimensional capturing space of the X-ray diagnostic apparatus 200 serves as the "one piece of second medical image data".

Specifically, the acquiring unit 221a acquires the three-dimensional position information of the landmark, based on "a position of the specific tissue in the one or the plurality of pieces of second medical image data" and based on "a landmark projection position, the landmark projection position being obtained by arranging the position of the landmark read from the output data in the three-dimensional capturing space and projecting the arranged position of the landmark onto the one or the plurality of pieces of second medical image data". Alternatively, the acquiring unit 221a acquires the three-dimensional position information of the landmark based on "a position of the specific tissue in the piece of second medical image data" and "a landmark projection position obtained by arranging the position of the landmark read from the output data in the three-dimensional capturing space and projecting the position of the landmark onto the piece of second medical image data".

In other words, the acquiring unit 221a associates the "specific tissue depicted in the second medical image data" with the "landmark" in the three-dimensional capturing space. The landmark is set at three or more points, which will be described later. By setting the landmark at three or more points, the association in the three-dimensional capturing space can be achieved using "a piece of second medical image data obtained by performing radiography in a capturing direction"

The following describes the case where the acquiring unit 221a acquires the three-dimensional position information of the landmark using "a plurality of pieces of X-ray image data obtained by performing contrast enhanced radiography". The contents described below are also applicable to the case where the acquiring unit 221a acquires the three-dimensional position information of the landmark using "a piece of X-ray image data obtained by performing contrast enhanced radiography". Still alternatively, the contents described below are also applicable to the case where "a plurality of pieces of X-ray image data captured in a plurality of capturing directions when the guide wire is inserted" is used as the "plurality of pieces of X-ray image data" and the case where "a piece of X-ray image data captured in a capturing direction when the guide wire is inserted" is used as the "piece of X-ray image data".

The acquiring unit 221a, for example, receives the output data and arranges the position of the specific tissue in each of the plurality of X-ray image data where the certain tissue (heart) of the subject P is captured from a plurality of directions and the position of the landmark read from the output data in a three-dimensional capturing space of the X-ray image data. The acquiring unit 221a then acquires three-dimensional position information based on the landmark projection position on which each of the plurality of X-ray image data is projected.

The display unit 223 included in the X-ray diagnostic apparatus 200 displays, based on the three-dimensional position information of the landmark, image data obtained by superimposing, on the second medical image data of the certain tissue, the first medical image data. Alternatively, the display unit 223 displays, based on the three-dimensional position information of the landmark, image data obtained by superimposing, on the second medical image data of the certain tissue, analysis image data, the analysis image data being generated by analyzing the first medical image data.

In the first embodiment, the display unit 223 displays image data obtained by superimposing, on the X-ray image data of the certain tissue (heart), analysis image data generated by analyzing the ultrasound image data based on the three-dimensional position information of the landmark.

The following describes an example of processing performed by the units illustrated in FIG. 9. FIG. 10, FIG. 11, and FIG. 12A to FIG. 12D are views for explaining an example of the landmark according to the first embodiment.

Figure 10:
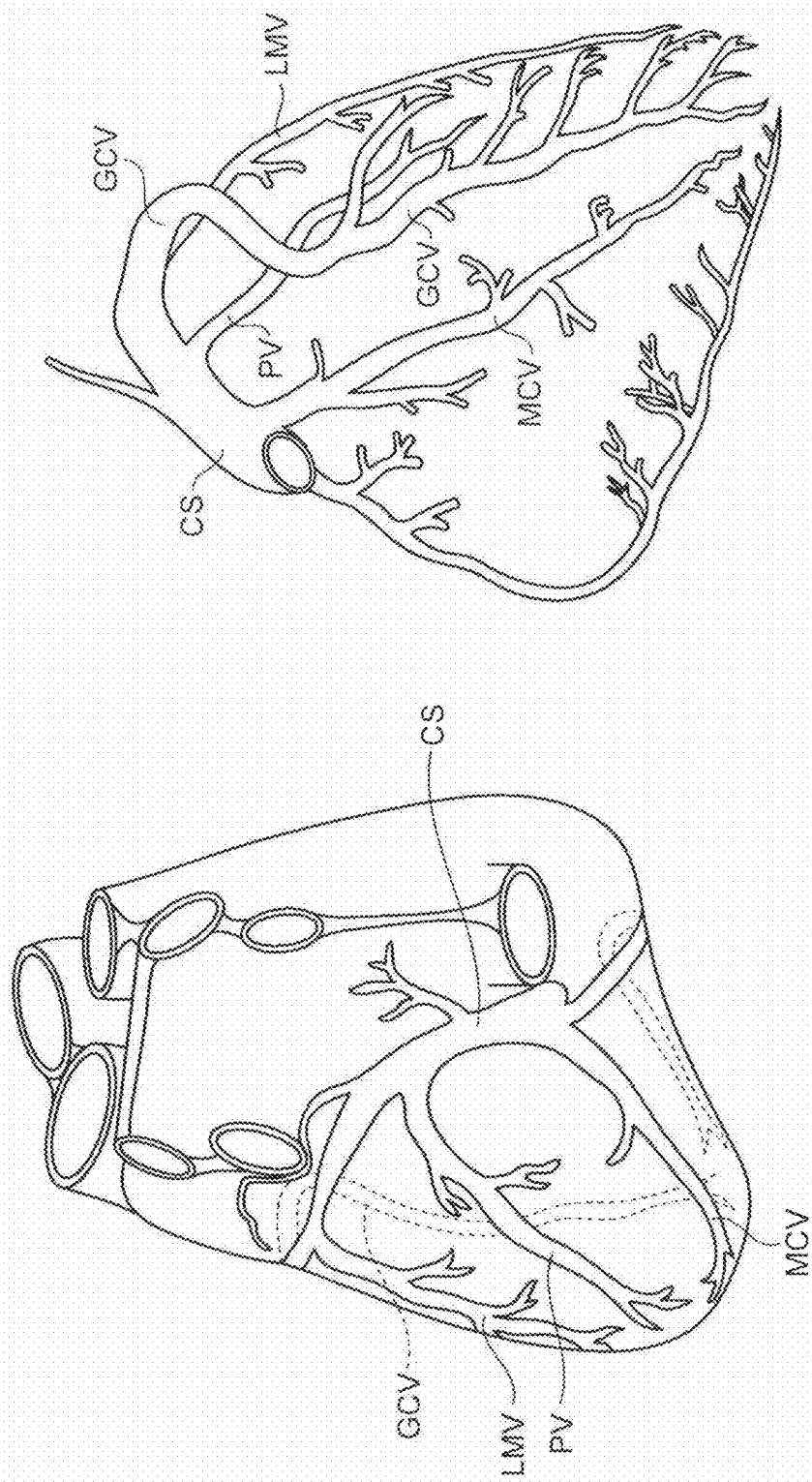
FIG. 10, FIG. 11, FIG. 12A, FIG. 12B, FIG. 12C and FIG. 12D are views for explaining a landmark according to the first embodiment.

As described above, an electrode is placed in a vein running around the heart in the CRT. In other words, the electrode is placed in the coronary vein. Specifically, the electrode is placed in the coronary vein running around the left ventricle. The left figure of FIG. 10 is a schematic of the coronary veins observed when the heart is viewed from the rear. The right figure of FIG. 10 is a schematic of the coronary veins observed when the heart is viewed from the front.

As illustrated in FIG. 10, the coronary veins gather at the coronary sinus (CS) positioned at the boundary between the left atrium and the left ventricle (left atrioventricular groove) and run toward the right atrium. As illustrated in FIG. 10, the great cardiac vein (GCV) runs from the boundary between the left ventricle and the right ventricle on the front side of the heart (anterior interventricular groove) and runs rearward along the left atrioventricular groove to join the CS. As illustrated in FIG. 10, the middle cardiac vein (MCV) runs along the boundary between the left ventricle and the right ventricle on the rear side of the heart (posterior interventricular groove) and joins the CS.

As illustrated in FIG. 10, the coronary veins running around the left ventricle include the left marginal vein of great cardiac vein (LMV) branching off from the GCV and the posterior veins of left ventricle (PV), for example. As illustrated in the left figure of FIG. 10, the GCV, the MCV, the LMV, and the PV run from the cardiac base toward the cardiac apex on the surface of the left ventricle. The doctor places the electrode at a position closest to the asynchronous area in a vein selected from these veins.

Figure 11:
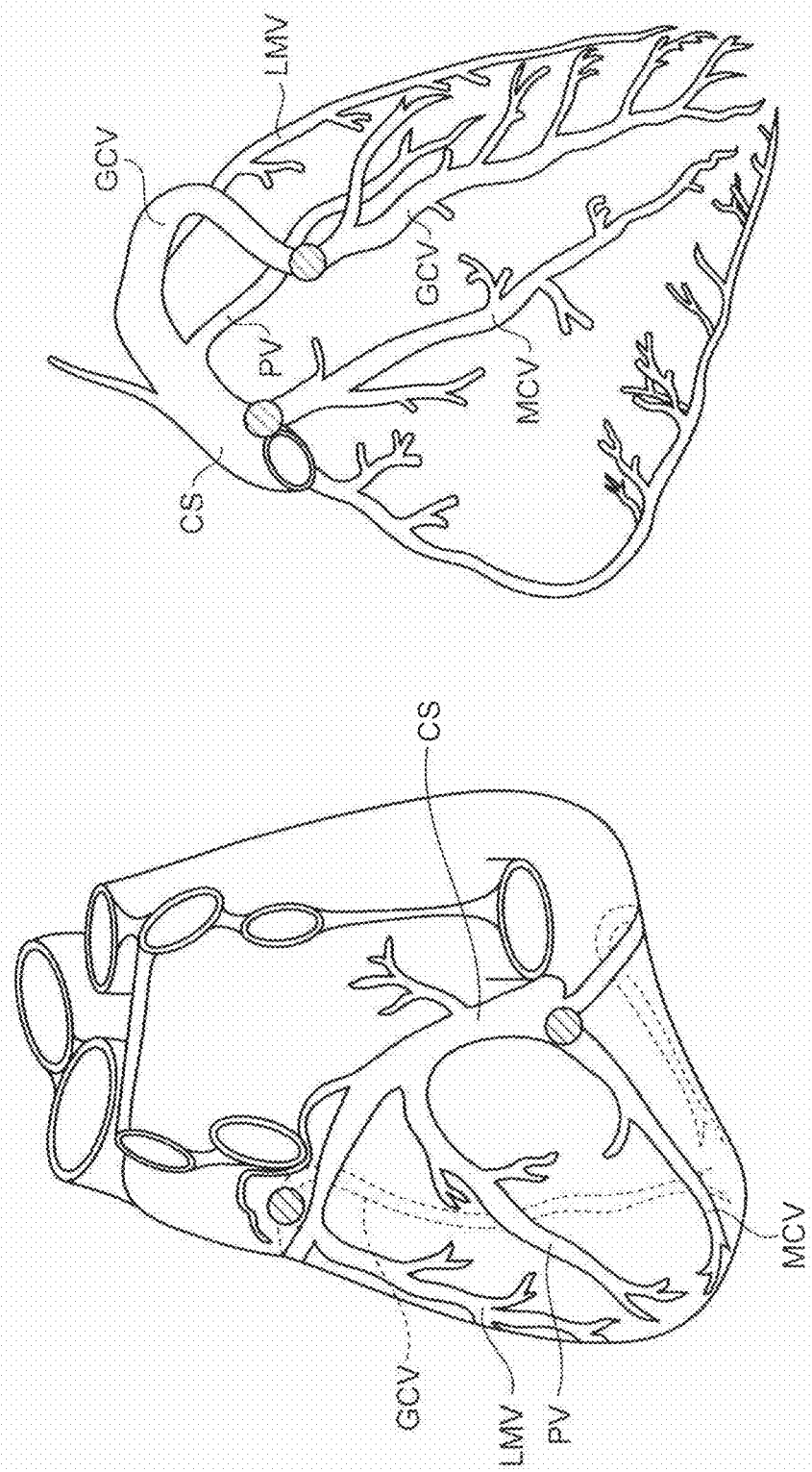

In X-ray image data generated by performing contrast enhanced radiography (X-ray contrast enhanced image data), the coronary veins can be found. In other words, the bifurcation of the CS and the GCV and the bifurcation of the CS and the MCV can be found in the X-ray contrast enhanced image data as illustrated in FIG. 11. Alternatively, the line along which the CS runs can be found in the X-ray contrast enhanced image data.

By contrast, it is difficult to find the coronary veins in observation of ultrasound image data. The CS, however, is positioned around the cardiac base as described above. The GCV branches off from the CS at the boundary between the left ventricle and the right ventricle on the front side of the heart, whereas the MCV branches off from the CS at the boundary between the left ventricle and the right ventricle on the rear side of the heart. The cardiac base and the boundary between the left ventricle and the right ventricle can be observed in B-mode ultrasound image data.

In other words, the position corresponding to the bifurcation of the CS and the GCV and the position corresponding to the bifurcation of the CS and the MCV can be found in the B-mode ultrasound image data. Alternatively, the line corresponding to the running line of the CS can be found in the B-mode ultrasound image data. In other words, an example of the specific tissue is the coronary veins running around the left ventricle (the CS, the GCV, and the MCV).

The input unit 130 receives, in the ultrasound image data constituting the ultrasound image data group used to generate the analysis image data, setting of the landmark at a position corresponding to the coronary vein. The input unit 130 according to the first embodiment receives setting of the landmark at a position corresponding to the coronary vein in two-dimensional image data, the two-dimensional image data being generated from three-dimensional ultrasound image data constituting the three-dimensional ultrasound image data group used to generate the three-dimensional analysis image data.

To put three-dimensional end-systolic analysis image data in the output data, for example, the operator inputs a display request of the three-dimensional end-systolic ultrasound image data to the input unit 130. The control unit 157 to which the display request is transferred reads three-dimensional ultrasound image data corresponding thereto from the image memory 155 and displays the three-dimensional ultrasound image data on the monitor 120. The control unit 157, for example, causes the image generating unit 154 to generate MPR image data by cutting the three-dimensional ultrasound image data on a C-plane at a plurality of levels and displays the MPR image data on the monitor 120. The operator refers to the monitor 120 to adjust the section such that the section is positioned at a cardiac base level. The operator, for example, moves the section positioned at a C7 level up and down and tilts the section positioned at the C7 level, thereby displaying MPR image data at the cardiac base level.

The operator refers to the MPR image data at the cardiac base level to set the landmark. The landmark is used to align the three-dimensional capturing space of the X-ray image data with the three-dimensional capturing space of the ultrasound image data. Consequently, the input unit 130 receives, as the landmark, "three or more points", "a line", or "two or more points and a line".

The operator, for example, refers to the MPR image data at the cardiac base level, thereby finding the position of the left atrioventricular groove, the boundary between the left ventricle (LV) and the right ventricle (RV) on the front side, and the boundary between the LV and the RV on the rear side.

Figure 12A:
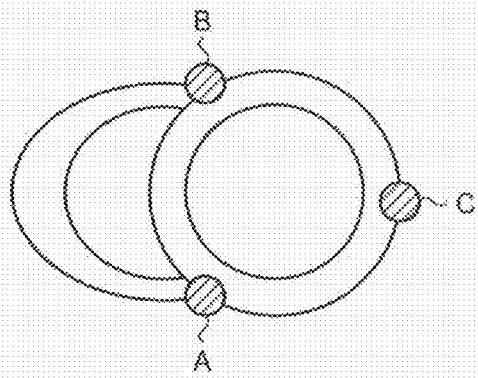

The input unit 130 receives setting of a point A at a position corresponding to the bifurcation of the CS and the GCV and receives setting of a point B at a position corresponding to the bifurcation of the CS and the MCV as illustrated in FIG. 12A, for example. Furthermore, the input unit 130 receives setting of a point C at a nearly intermediate point between the point A and the point B in the left atrioventricular groove on the free wall side as illustrated in FIG. 12A, for example.

Figure 12B:
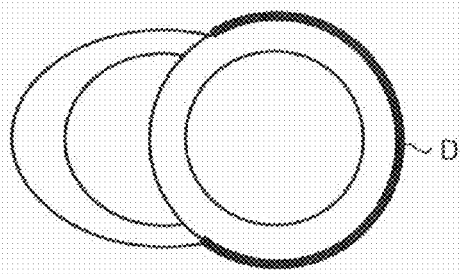

Alternatively, the input unit 130 receives setting of a line (line D) corresponding to the running line of the CS and having a constant thickness in the left atrioventricular groove on the free wall side as illustrated in FIG. 12B, for example.

Figure 12C:
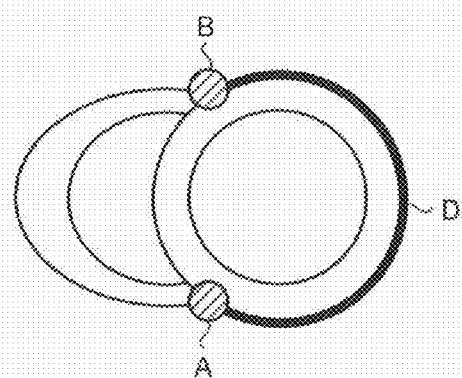

Alternatively, the input unit 130 receives setting of the point A, point B, and the line D as illustrated in FIG. 12C, for example. The line D set in the case of FIG. 12C may not include the point A and the point B.

Figure 12D:
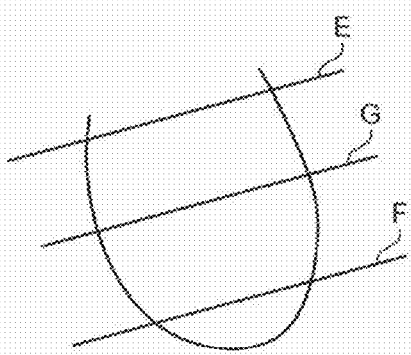

The MPR image data on which the landmark is set is not limited to MPR image data at the cardiac base level. As illustrated in FIG. 12D, the MPR image data on which the landmark is set may be MPR image data of "a section E corresponding to the cardiac base level", MPR image data of "a section F corresponding to a level closer to a cardiac apex level", and MPR image data of "a section G positioned at a level intermediate between the section E and the section F", for example. In such a case, any one of the landmarks described with reference to FIG. 12A, FIG. 12B, and FIG. 12C is set in the three pieces of MPR image data.

The position of the landmark illustrated in FIG. 12A to FIG. 12C is converted, by processing of the output unit 157a, into coordinates in the three-dimensional space of the three-dimensional ultrasound image data from which the MPR image is generated. The output unit 157a uses the ultrasound image data, the analysis image data, or synthetic data of the ultrasound image data and the analysis image data as analysis result data. In the first embodiment, the output unit 157a uses, as the analysis result data, the three-dimensional ultrasound image data, the three-dimensional analysis image data, both the three-dimensional ultrasound image data and the three-dimensional analysis image data, or three-dimensional synthetic data of the three-dimensional ultrasound image data and the three-dimensional analysis image data.

The three-dimensional ultrasound image data is three-dimensional ultrasound image data at the time phase of the three-dimensional analysis image data. The three-dimensional ultrasound image data is three-dimensional end-systolic ultrasound image data corresponding to three-dimensional end-systolic analysis image data, for example. The three-dimensional analysis image data is the three-dimensional analysis image data described with reference to FIG. 6, for example.

The output unit 157a outputs data obtained by adding the information of the position of the landmark in the analysis result data to the analysis result data as output data. In the present embodiment, the output unit 157a outputs the output data to the X-ray diagnostic apparatus 200.

Figure 13A:
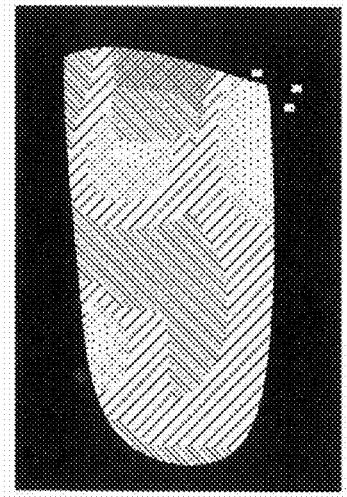
FIG. 13A, FIG. 13B and FIG. 13C are views of an example of output data according to the first embodiment.
Figure 13B:
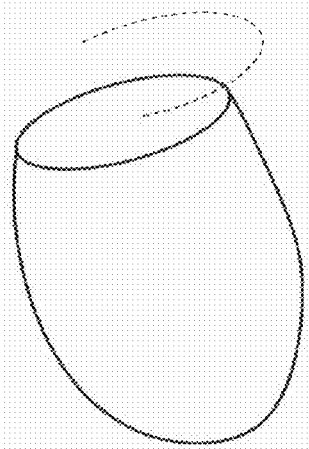
Figure 13C:
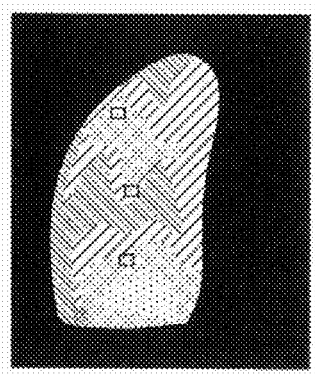

FIG. 13A, FIG. 13B, and FIG. 13C are views of an example of the output data according to the first embodiment. The output unit 157a outputs data obtained by adding the information of the position of the landmark (three points illustrated in FIG. 12A) in the three-dimensional analysis image data to the three-dimensional analysis image data as illustrated in FIG. 13A, for example.

Alternatively, the output unit 157a outputs data obtained by adding the information of the position of the landmark (a line illustrated in FIG. 12B) in the three-dimensional analysis image data to the three-dimensional analysis image data as illustrated in FIG. 13B, for example. Still alternatively, if one landmark is set on each of the sections at the three levels as described with reference to FIG. 12D, the output unit 157a outputs data obtained by adding the information of the positions of the landmarks (three points) in the three-dimensional analysis image data to the three-dimensional analysis image data as illustrated in FIG. 13C.

Thus, the acquiring unit 221a of the X-ray diagnostic apparatus 200 receives the output data. The acquiring unit 221a uses the output data to align the three-dimensional capturing space of the X-ray image data with the three-dimensional capturing space of the ultrasound image data. FIG. 14, FIG. 15, FIG. 16A, and FIG. 16B are views for explaining the acquiring unit according to the first embodiment.

Figure 14:
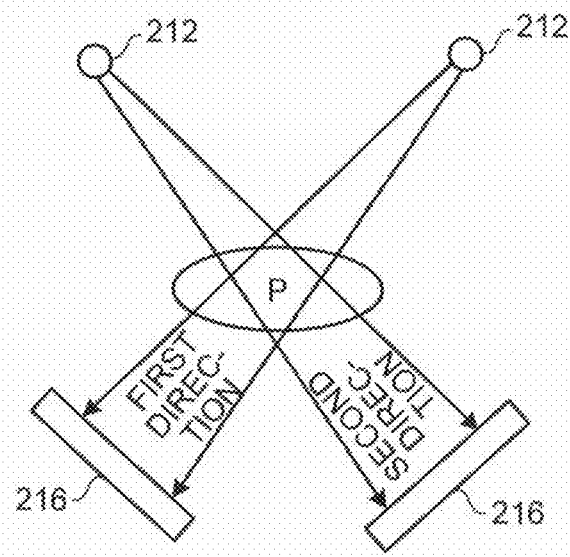
FIG. 14, FIG. 15, FIG. 16A, and FIG. 16B are views for explaining an acquiring unit according to the first embodiment.

Based on the control of the acquiring unit 221a, the X-ray diagnostic apparatus 200 performs contrast enhanced radiography on the heart of the subject P in a plurality of directions, thereby generating a plurality of pieces of X-ray image data. Based on the control of the acquiring unit 221a, the X-ray tube 212 irradiates the subject P with an X-ray in a first direction, and the X-ray detector 216 detects the X-ray passing through the subject P in the first direction as illustrated in FIG. 14, for example. Thus, the image data generating unit 224 generates first-direction X-ray image data. Furthermore, based on the control of the acquiring unit 221a, the X-ray tube 212 irradiates the subject P with an X-ray in a second direction, and the X-ray detector 216 detects the X-ray passing through the subject P in the second direction as illustrated in FIG. 14, for example. Thus, the image data generating unit 224 generates second-direction X-ray image data.

Figure 15:
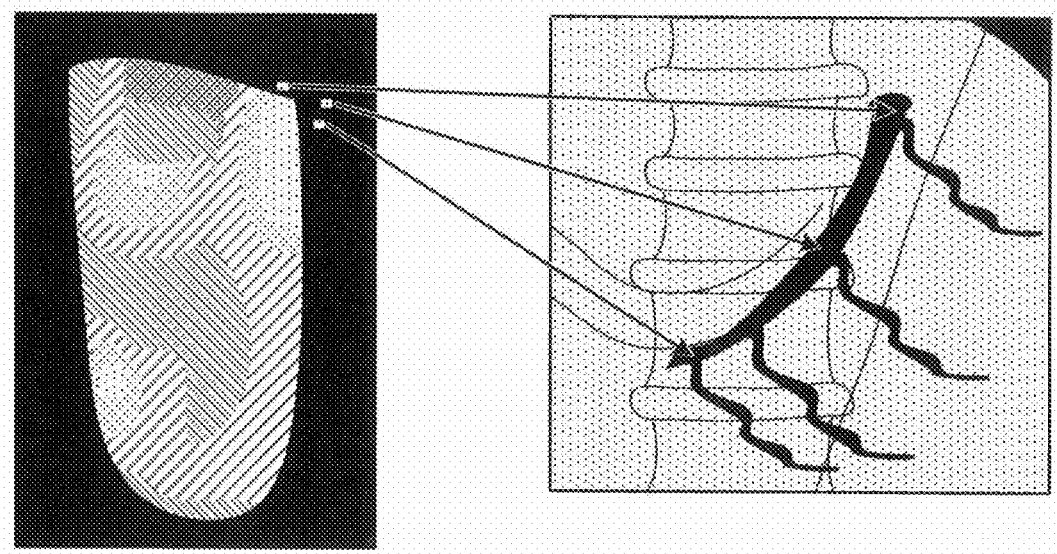

The acquiring unit 221a uses the first-direction X-ray image data, the second-direction X-ray image data, and the output data, thereby acquiring the three-dimensional position information of the landmark. As illustrated in FIG. 15, the acquiring unit 221a associates the landmark formed of three points in the three-dimensional analysis image data with the coronary vein depicted in the X-ray contrast enhanced image data, thereby acquiring the three-dimensional position information of the landmark, for example.

The acquiring unit 221a arranges the three-dimensional analysis image data serving as the analysis result data in the three-dimensional capturing space of the X-ray diagnostic apparatus 200. The acquiring unit 221a acquires the landmark projection position in each of the plurality of pieces of X-ray image data. The position at which the analysis result data is arranged is set by the operator, for example. Alternatively, the arrangement position is a preset position, for example. The acquiring unit 221a, for example, projects the landmark formed of three points in the three-dimensional analysis image data arranged in the three-dimensional capturing space in the first direction and the second direction.

The acquiring unit 221a acquires the projection positions of the three points in the first-direction X-ray image data. The image processing unit 226 depicts points (marks) at the respective three projection points acquired by the acquiring unit 221a in the first-direction X-ray image data. Similarly, the acquiring unit 221a acquires the projection positions of the three points in the second-direction X-ray image data. The image processing unit 226 depicts points (marks) at the respective three projection points acquired by the acquiring unit 221a in the second-direction X-ray image data.

Based on the control of the acquiring unit 221a, the display unit 223 displays the landmark projection positions in the plurality of pieces of X-ray image data. As illustrated in the left figure of the FIG. 16A, the display unit 223 displays the first-direction X-ray image data in which three points are depicted at positions where the landmark formed of three points is projected in the first direction, for example. Furthermore, as illustrated in the left figure of the FIG. 16B, the display unit 223 displays the second-direction X-ray image data in which three points are depicted at positions where the landmark formed of three points is projected in the second direction, for example.

The acquiring unit 221a acquires the three-dimensional position information of the landmark based on an operation for associating the landmark projection positions with the positions of the specific tissue (coronary vein) in the plurality of pieces of X-ray image data, the operation being performed by the operator who refers to the display unit 223.

Figure 16A:
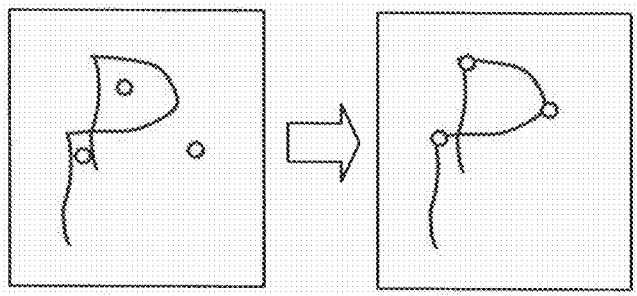

The operator refers to the image illustrated in the left figure of FIG. 16A to move the three points depicted in the image to the respective points corresponding thereto on the coronary vein, for example. As a result, the three landmark projection positions are associated with the bifurcation of the CS and the GCV, the point on the CS, and the bifurcation of the CS and the MCV depicted in the first-direction X-ray image data as illustrated in the right figure of FIG. 16A.

Figure 16B:
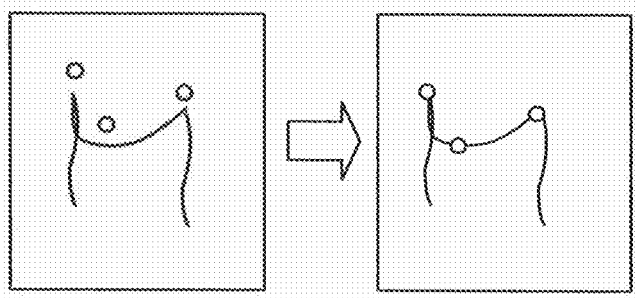

Furthermore, the operator refers to the image illustrated in the left figure of FIG. 16B to move each of the three points depicted in the image to the respective points corresponding thereto on the coronary vein, for example. As a result, the three landmark projection positions are associated with the bifurcation of the CS and the GCV, the point on the CS, and the bifurcation of the CS and the MCV depicted in the second-direction X-ray image data as illustrated in the right figure of FIG. 16B.

The operator performs the moving operation such that the landmark thus projected substantially coincides with the landmark depicted in the X-ray image data. In the case where the landmark is a line, the operator performs the moving operation such that a large part of the line thus projected coincides with the running line of the CS. The points of the projected landmark may possibly not be found in the X-ray image data depending on the projection direction. In view of such a case, the landmark is preferably set as a line having a thickness or as two or more points on each of the plurality of sections as described with reference to FIG. 12D. Alternatively, the projection direction of the X-ray image data may be adjusted such that the points of the projected landmark can be found on the X-ray image data.

Besides the landmark, the analysis result data may be projected in the present embodiment. In other words, the three-dimensional ultrasound image data, the three-dimensional analysis image data, or the synthetic data of these data, which is the analysis result data, may be projected on the plurality of pieces of X-ray image data. Carrying out such processing enables the operator to perform association of the landmark projection positions while checking the left atrioventricular groove, the anterior interventricular groove, and the posterior interventricular groove, for example. The association of the landmark projection positions may be performed using unidirectional X-ray image data as described above.

The acquiring unit 221a performs translation and rotation of the landmark arranged in the three-dimensional capturing space based on the amount of movement and the direction of movement of the landmark projection positions. The acquiring unit 221a then acquires the position of the landmark subjected to the processing as the three-dimensional position information of the landmark. Along with the translation and the rotation of the landmark, the three-dimensional analysis image data is also translated and rotated in the three-dimensional capturing space. The moving operation may possibly change the distance between the landmarks. In such a case, the acquiring unit 221a changes the distance between the landmarks in the three-dimensional capturing space. If such processing is performed, the three-dimensional analysis image data is expanded, reduced, or deformed in the three-dimensional capturing space.

The image processing unit 226 projects the three-dimensional analysis image data rearranged in the three-dimensional capturing space based on the three-dimensional position information of the landmark or the three-dimensional analysis image data rearranged in the three-dimensional capturing space based on the three-dimensional position information of the landmark and then "expanded, reduced, or deformed" on the X-ray image data of the heart of the subject P being captured in real time in a direction desired by the doctor. In other words, the image processing unit 226 generates image data by superimposing the projection image of the three-dimensional analysis image data aligned in the three-dimensional capturing space on the X-ray image data of the heart. The direction desired by the doctor is a direction for capturing X-ray image data suitably used to place the electrode. The direction desired by the doctor can be arbitrarily changed during an operation. The image processing unit 226 projects the three-dimensional analysis image data on the X-ray image data of the heart of the subject P being captured in real time in the direction thus changed.

Figure 17:
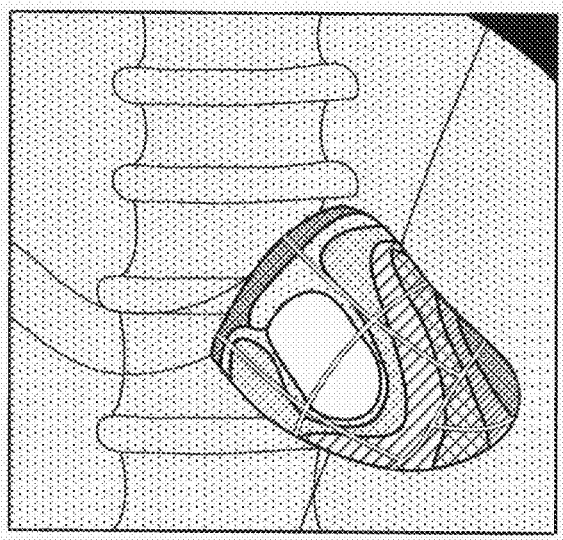
FIG. 17 is a view of an example of image data displayed in the first embodiment.

FIG. 17 is a view of an example of image data displayed in the first embodiment. By referring to the image data illustrated in FIG. 17, the doctor can place the electrode into a vein closest to the asynchronous area while checking the asynchronous area in the projection image of the three-dimensional analysis image data. Because the projection image of the three-dimensional analysis image data is a superimposed image, display and non-display thereof are switchable in response to a request from the operator. In the present embodiment, the projection target of the three-dimensional analysis image data to be superimposed on the X-ray image data may only be the asynchronous area. The opacity of the projection image of the three-dimensional analysis image data to be superimposed can be arbitrarily changed. The X-ray image data on which the projection image of the three-dimensional analysis image data is superimposed may be X-ray contrast enhanced image data or X-ray non-contrast image data.

In the case where the analysis result data is three-dimensional ultrasound image data, the acquiring unit 221a acquires the three-dimensional position information of the landmark and then acquires the three-dimensional analysis image data corresponding thereto from the ultrasonic diagnostic apparatus 100. Alternatively, in the case where the analysis result data is three-dimensional ultrasound image data, the image data superimposed on the X-ray image data captured in the direction desired by the doctor may be image data generated based on the three-dimensional ultrasound image data besides the projection image of the three-dimensional analysis image data. The image data generated based on the three-dimensional ultrasound image data is ultrasound image data having a plurality of short-axis planes including a short-axis plane of the asynchronous area, for example.

Figure 18:
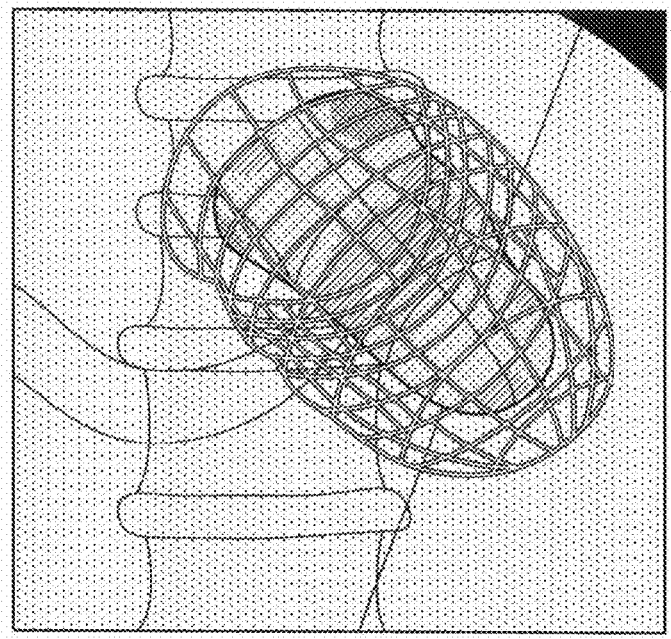
FIG. 18 is a view for explaining a modification according to the first embodiment.

To acquire the three-dimensional position information of the landmark, the present embodiment may use information other than the landmark set by the operator. FIG. 18 is a view for explaining a modification according to the first embodiment. Specifically, the output unit 157a may add at least epicardium position information to the output data as shape information of a heart serving as the certain tissue and output the output data. In such a case, the output unit 157a adds the epicardium position information to the output data as the shape information and outputs the output data. Specifically, the epicardium position information is three-dimensional wire frame data of the epicardium obtained by the 3DT, whereas endocardium position information is three-dimensional wire frame data of the endocardium obtained by the 3DT. The present embodiment may add the endocardium position information to the output data.

The display unit 223 displays an epicardium projection position obtained by projecting the epicardium position information onto each of the plurality of pieces of X-ray image data together with the landmark projection positions. As illustrated in FIG. 18, the display unit 223 displays data obtained by projecting the three-dimensional wire frame data of the epicardium in the first direction in a manner superimposed on the first-direction X-ray image data, for example.

The acquiring unit 221a acquires the three-dimensional position information of the landmark further based on an operation for associating the epicardium projection position with a predetermined position of an epicardium in each of the plurality of pieces of X-ray image data, the operation being performed by the operator who refers to the display unit 223. The predetermined position of the epicardium is the cardiac apex of the left ventricle. While the cardiac apex is not clearly depicted in the X-ray image data, the operator can visually identify the cardiac apex. In the present modification, the operator moves the cardiac apex found in the projection image of the three-dimensional wire frame data of the epicardium to the cardiac apex found in the X-ray image data. Thus, the present modification can acquire the three-dimensional position information of the landmark more accurately. The projection image of the three-dimensional wire frame data of the endocardium can be used as auxiliary information for checking the left atrioventricular groove, the anterior interventricular groove, and the posterior interventricular groove, for example.

In the present modification, the output unit 157a outputs the epicardium position information as specific information, display and non-display of the specific information being switchable. Specifically, the output unit 157a outputs the specific information as information represented by a predetermined brightness value. The output unit 157a, for example, outputs the analysis result data as data represented by a brightness value of 511 gray-scale out of 512 gray-scale and outputs the epicardium position information as data represented by a brightness value of one gray-scale out of the 512 gray-scale. This can facilitate switching of display and non-display of the epicardium position information. If the epicardium projection position is displayed, it may possibly be difficult to align the landmark projection positions. By adding the epicardium position information having the structure described above to the output data, it is possible to perform alignment of the landmark projection positions smoothly.

If no epicardium position information is used and three-dimensional synthetic data is used as the analysis result data, the output unit 157a may output the three-dimensional analysis image data as data represented by a brightness value of 511 gray-scale out of the 512 gray-scale and output the three-dimensional ultrasound image data as data represented by a brightness value of one gray-scale out of the 512 gray-scale. This can facilitate switching of display and non-display of the three-dimensional ultrasound image data.

Figure 19:
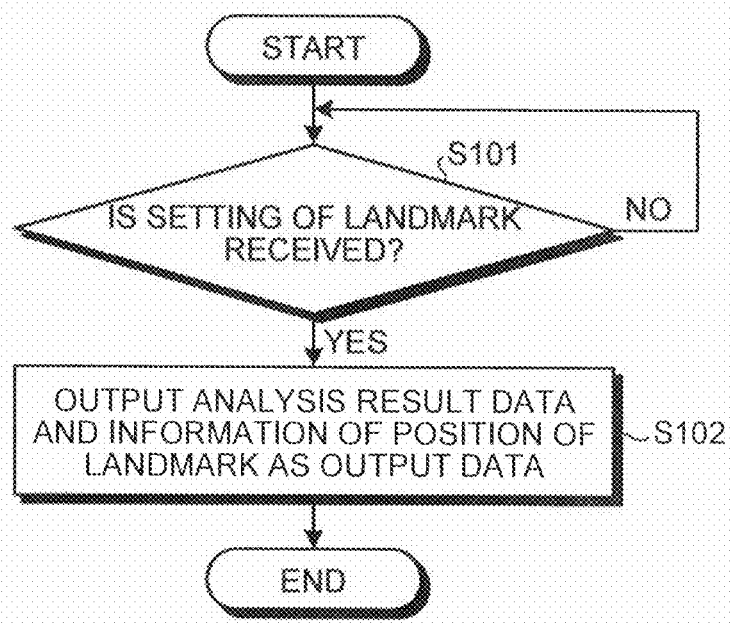
FIG. 19 is a flowchart for explaining an example of processing performed by the ultrasonic diagnostic apparatus according to the first embodiment.

The following describes a flow of the processing of the image processing system 1 according to the first embodiment with reference to FIG. 19 and FIG. 20. FIG. 19 is a flowchart for explaining an example of the processing performed by the ultrasonic diagnostic apparatus according to the first embodiment. FIG. 20 is a flowchart for explaining an example of the processing performed by the X-ray diagnostic apparatus according to the first embodiment. FIG. 19 illustrates an example of processing performed after the MPR image data of the three-dimensional ultrasound image data is displayed and the three-dimensional analysis image data is generated.

As illustrated in FIG. 19, the input unit 130 included in the ultrasonic diagnostic apparatus 100 according to the first embodiment determines whether setting of a landmark is received from the operator (Step S101). If no setting of a landmark is received (No at Step S101), the input unit 130 waits until setting of a landmark is received.

By contrast, if setting of a landmark is received (Yes at Step S101), the output unit 157a outputs analysis result data and information of the position of the landmark as output data (Step S102). The processing is then terminated.

As illustrated in FIG. 20, the acquiring unit 221a included in the X-ray diagnostic apparatus 200 according to the first embodiment determines whether output data is received from the ultrasonic diagnostic apparatus 100 (Step S201). If no output data is received (No at Step S201), the acquiring unit 221a waits until output data is received.

By contrast, if output data is received (Yes at Step S201), the acquiring unit 221a controls each unit of the X-ray diagnostic apparatus 200 so as to generate a plurality of pieces of X-ray image data in a plurality of directions (Step S202). Specifically, the X-ray diagnostic apparatus 200 captures the heart of the subject P into which a contrast medium is injected in a plurality of directions.

Based on the control of the acquiring unit 221a, the display unit 223 displays the landmark projection position in a manner superimposed on the plurality of pieces of X-ray image data (Step S203). The acquiring unit 221a determines whether an associating operation for associating the landmark projection position with the position of the specific tissue in the plurality of pieces of X-ray image data is received from the operator (Step S204). If no associating operation is received (No at Step S204), the acquiring unit 221a waits until an associating operation is received.

By contrast, if an associating operation is received (Yes at Step S204), the acquiring unit 221a acquires the three-dimensional position information of the landmark in the three-dimensional capturing space based on the associating operation (Step S205). Based on the control of the acquiring unit 221a, the display unit 223 displays image data obtained by aligning the analysis image data with the X-ray image data (Step S206). The processing is then terminated.

As described above, the first embodiment aligns the ultrasound image data with the X-ray image data using the coronary vein, which is the specific tissue that can be readily identified in the X-ray image data by contrast enhanced radiography and that is not depicted in the ultrasound image data but whose existing position can be identifiable because of its tissue shape. Thus, the first embodiment makes it possible to identify the area specified in the ultrasonic diagnosis under X-ray fluoroscopic guidance. In the first embodiment, the doctor can place the electrode near the asynchronous area while referring to the projection image of the three-dimensional analysis image data made available for superimposed display by the alignment.

Second Embodiment

A second embodiment will describe the case where the analysis image data is two-dimensional data with reference to FIG. 21A, FIG. 21B, FIG. 22, and FIG. 23. FIG. 21A, FIG. 21B, FIG. 22, and FIG. 23 are views for explaining the second embodiment.

An image processing system 1 according to the second embodiment has the same configuration as that of the image processing system 1 according to the first embodiment explained with reference to FIG. 1. The second embodiment is also applicable to the case where an ultrasonic diagnostic apparatus 100 is an apparatus used exclusively for two-dimensional scanning.

Figure 21A:
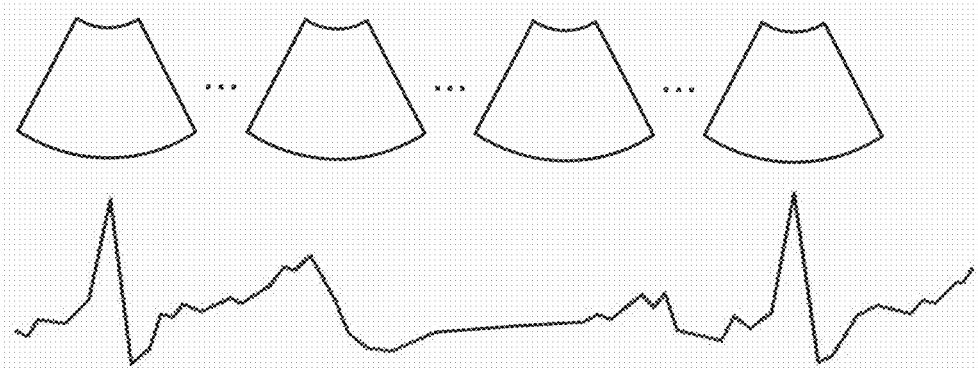
FIG. 21A, FIG. 21B, FIG. 22 and FIG. 23 are views for explaining a second embodiment.

Specifically, an analyzing unit 156 according to the second embodiment analyzes a two-dimensional ultrasound image data group in a time series generated by performing two-dimensional ultrasonic scanning on the subject P to generate two-dimensional analysis image data. In the second embodiment, the operator performs two-dimensional scanning on a short-axis section of the left side of the heart of the subject P for a time period equal to or longer than one heartbeat. As a result, an image generating unit 154 generates a plurality of pieces of time-series two-dimensional ultrasound image data in a time period equal to or longer than one heartbeat as illustrated in FIG. 21A and stores the plurality of pieces of two-dimensional ultrasound image data in an image memory 155. The plurality of pieces of two-dimensional ultrasound image data stored in the image memory 155 are a two-dimensional ultrasound image data group generated by performing ultrasonic scanning on the short-axis section of the heart including at least the left ventricle for a time period equal to or longer than one heartbeat. The two-dimensional ultrasound image data according to the second embodiment is two-dimensional B-mode image data. The second embodiment may perform the two-dimensional scanning using an ultrasound probe 110, which is a mechanical 4D probe or a 2D array probe, or the ultrasound probe 110 used exclusively for two-dimensional scanning.

The analyzing unit 156 derives time-series data of the heart wall motion information from the two-dimensional ultrasound image data group. Specifically, the analyzing unit 156 uses the result of tracking of tracking points performed by processing including pattern matching between the plurality of pieces of two-dimensional ultrasound image data, thereby deriving the heart wall motion information. In the second embodiment, 2D speckle tracking (hereinafter, referred to as "2DT") is performed.

An input unit 130, for example, receives a display request of the first frame of the two-dimensional ultrasound image data group from the operator. A control unit 157 to which the display request is transferred reads two-dimensional ultrasound image data of the first frame from the image memory 155 and displays the two-dimensional ultrasound image data on a monitor 120.

Figure 21B:
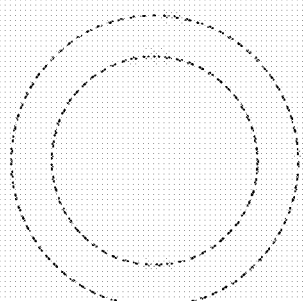

The operator refers to the two-dimensional ultrasound image data displayed on the monitor 120, thereby setting a plurality of tracking points used to perform 2DT. The operator, for example, traces the positions of the endocardium of the left ventricle and the epimyocardium in the two-dimensional ultrasound image data. The analyzing unit 156 reconstructs a two-dimensional boundary surface from the endocardial surface and the epicardial surface thus traced. The analyzing unit 156 sets a plurality of tracking points formed in pairs in the endocardial surface and the epicardial surface of the first frame as illustrated in FIG. 21B. The analyzing unit 156 sets template data to each of the plurality of tracking points set in the first frame. The template data is formed of a plurality of pixels around each tracking point.

The analyzing unit 156 searches for an area that is the most identical to the speckle pattern of the template data between two frames, thereby tracking to which position the template data moves in the next frame. The tracking points may be set by the analyzing unit 156 detecting the endocardial surface and the epicardial surface of the left ventricle included in the first frame.

Thus, the analyzing unit 156 derives the time-series data of the heart wall motion information, such as strain and displacement. The analyzing unit 156 derives strain as the heart wall motion information from the result of the 2DT of the endocardium and the epicardium, for example. The analyzing unit 156 derives strain in the circumferential direction and strain in the radial direction. Alternatively, the analyzing unit 156 derives displacement from the result of the 2DT of the endocardium or the epicardium. The analyzing unit 156 derives displacement in the circumferential direction, strain in the circumferential direction in the radial direction, and strain in the radial direction.

The analyzing unit 156, for example, converts the values of the heart wall motion information of 16 segments into color scales and maps the values between the endocardial surface and the epicardial surface in the two-dimensional ultrasound image data, thereby generating two-dimensional analysis image data. In other words, the two-dimensional analysis image data generated by the analyzing unit 156 according to the second embodiment corresponds to the analysis image data of the C-plane illustrated in FIG. 7.

The input unit 130 according to the second embodiment receives setting of the landmark in two-dimensional ultrasound image data constituting the two-dimensional ultrasound image data group. If two-dimensional end-systolic analysis image data is selected, for example, the landmark is set in the two-dimensional end-systolic ultrasound image data. The input unit 130, for example, receives a landmark formed of two points and a line having a thickness explained with reference to FIG. 12C in the first embodiment (refer to the left figure of FIG. 22).

The output unit 157a according to the second embodiment uses, as analysis result data, the two-dimensional ultrasound image data, the two-dimensional analysis image data, both the two-dimensional ultrasound image data and the two-dimensional analysis image data, or two-dimensional synthetic data of the two-dimensional ultrasound image data and the two-dimensional analysis image data. The output unit 157a outputs data obtained by adding the information of the position of the landmark in the analysis result data to the analysis result data as output data. The following describes the case where a two-dimensional synthetic data serves as the analysis result data, the two-dimensional synthetic data being synthetic data of the two-dimensional ultrasound image data and the two-dimensional analysis image data obtained by color-mapping of the values of the heart wall motion information between the endocardial surface and the epicardial surface in the two-dimensional ultrasound image data.

Figure 22:
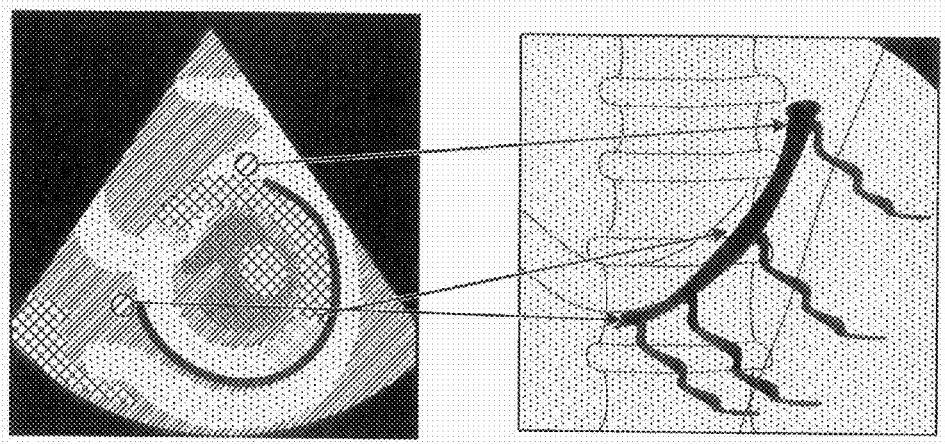

As described in the first embodiment, an acquiring unit 221a according to the second embodiment acquires the three-dimensional position information of the landmark based on a plurality of pieces of X-ray image data captured in a plurality of directions and the landmark projection position. In other words, the acquiring unit 221a acquires the three-dimensional position information of the landmark by associating the landmark formed of two points and a line in the two-dimensional analysis image data with the coronary vein depicted in the X-ray contrast enhanced image data as illustrated in FIG. 22. Also in the second embodiment, the acquiring unit 221a may acquire the three-dimensional position information of the landmark based on a piece of X-ray image data captured in a direction and the landmark projection position.

Similarly to the first embodiment, the second embodiment arranges the two-dimensional analysis image data in the three-dimensional capturing space and then projects the landmark onto first-direction X-ray image data and second-direction X-ray image data, for example. Also in the second embodiment, the operator performs an operation such that the landmark projection position coincides with the coronary vein depicted in the X-ray contrast enhanced image data as illustrated in the left figure of FIG. 23. As a result, the position of the landmark in the three-dimensional capturing space is modified, and the position of the two-dimensional analysis image data in the three-dimensional capturing space is modified. Also in the second embodiment, the operation of the operator may possibly deform the two-dimensional analysis image data.

Figure 23:
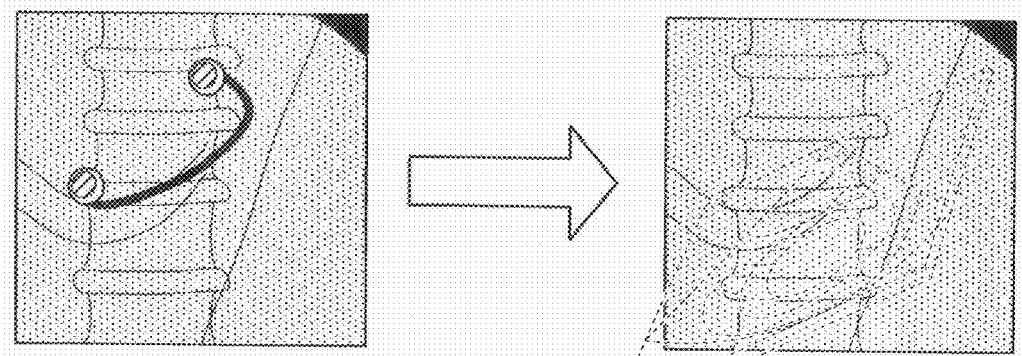

Also in the second embodiment, a display unit 223 displays image data in which the two-dimensional analysis image data is superimposed on the X-ray image data of the heart as illustrated in the right figure of FIG. 23 by projecting the two-dimensional analysis image data rearranged in the three-dimensional capturing space in a direction desired by the doctor. In the example illustrated in the right figure of FIG. 23, the projection image of the two-dimensional synthetic data is superimposed and displayed in a manner aligned with the X-ray image data. In the second embodiment, the image data superimposed and displayed in a manner aligned with the X-ray image data may be ultrasound image data on the short-axis plane of the asynchronous area, for example.

Because the flow of the processing according to the second embodiment is the same as that of the first embodiment except that the analysis image data is two-dimensional data, the explanation thereof will be omitted. The contents described in the first embodiment are also applied to the second embodiment as much as possible except that the analysis image data is two-dimensional data.

As described above, the second embodiment can align ultrasound image data with X-ray image data using the ultrasonic diagnostic apparatus 100 capable of performing processing of two-dimensional data only. Because the projection image made available for superimposed display by the alignment is the projection image of the two-dimensional analysis image data in the second embodiment, a wide range of the asynchronous area fails to be checked. The doctor, however, can check a vein close to the asynchronous area, thereby placing the electrode into a position at which a large therapeutic effect is achieved compared with the conventional technology.

Third Embodiment

Figure 24:
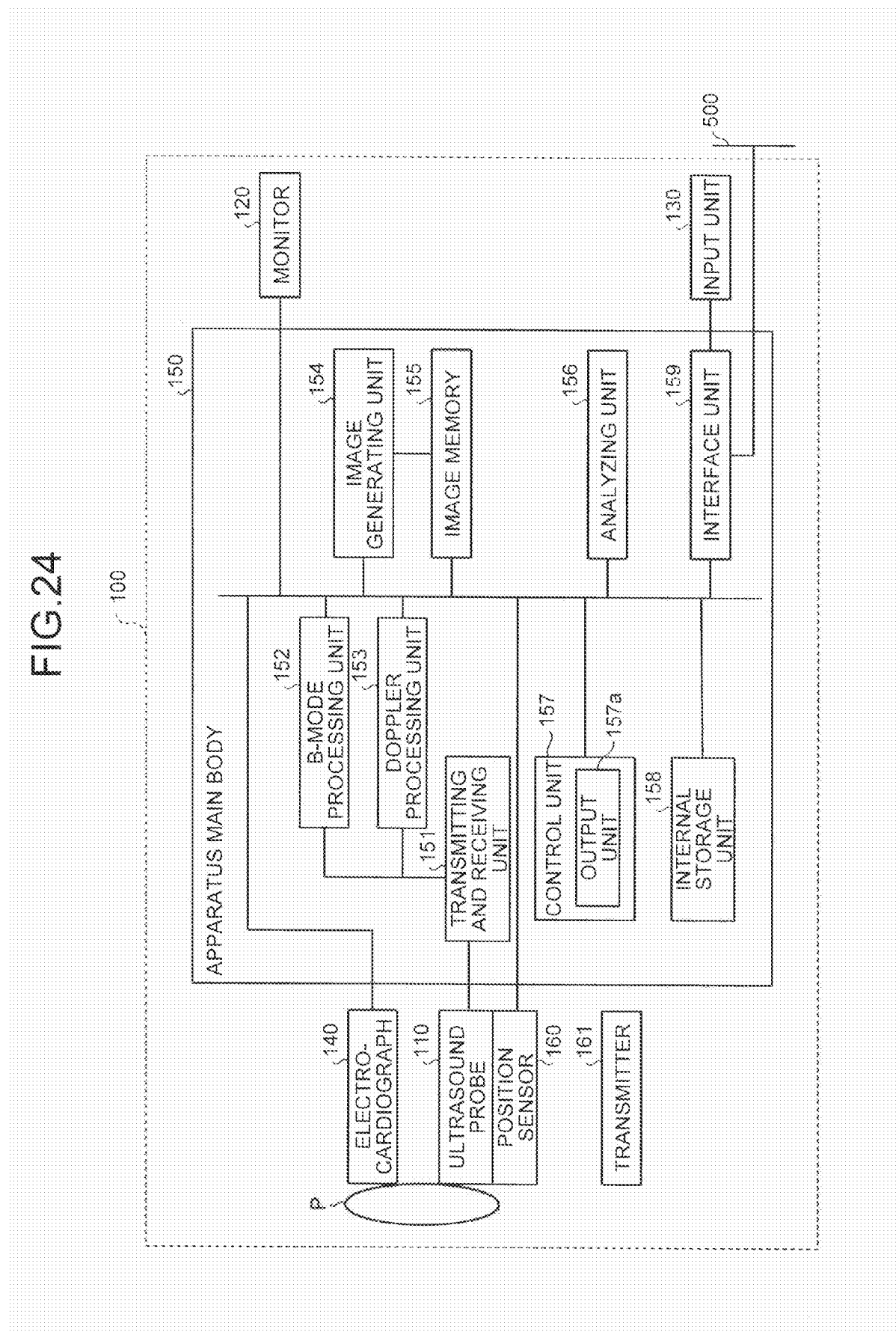
FIG. 24 is a block diagram of an exemplary configuration of an ultrasonic diagnostic apparatus according to a third embodiment.

A third embodiment will describe the case where the two-dimensional analysis image data is generated on a plurality of sections with reference to FIG. 24, FIG. 25A, FIG. 25B, FIG. 25C, and FIG. 26. FIG. 24 is a block diagram of an exemplary configuration of an ultrasonic diagnostic apparatus according to the third embodiment. FIG. 25A, FIG. 25B, FIG. 25C, and FIG. 26 are views for explaining the third embodiment.

An image processing system 1 according to the third embodiment has the same configuration as that of the image processing system 1 according to the first embodiment explained with reference to FIG. 1. In an ultrasonic diagnostic apparatus 100 according to the third embodiment, a position sensor 160 is attached to an ultrasound probe 110, and a transmitter 161 is provided as illustrated in FIG. 24 unlike the ultrasonic diagnostic apparatus 100 according to the first embodiment.

The position sensor 160 and the transmitter 161 are devices that acquire the position information of the ultrasound probe 110. The position sensor 160 is a magnetic sensor attached to the ultrasound probe 110, for example. The transmitter 161 is arranged at an arbitrary position and generates a magnetic field extending outward from the transmitter 161 with the transmitter 161 being the center.

The position sensor 160 detects the three-dimensional magnetic field generated by the transmitter 161. The position sensor 160 derives the position (coordinates and an angle) of the position sensor 160 in a space with its origin at the transmitter 161 based on the information of the magnetic field thus detected and transmits the position thus derived to the apparatus main body 150. The position sensor 160 transmits the three-dimensional coordinates and angle at which the position sensor 160 is positioned to the apparatus main body 150 as the three-dimensional position information of the ultrasound probe 110. Specifically, the position sensor 160 transmits the three-dimensional position information of the ultrasound probe 110 to an output unit 157a.

The present embodiment is also applicable to the case where the position information of the ultrasound probe 110 is acquired by a system other than the position detecting system using the position sensor 160 and the transmitter 161. The present embodiment may acquire the position information of the ultrasound probe 110 using a gyro sensor and an acceleration sensor, for example.

In the third embodiment, an analyzing unit 156 analyzes a plurality of two-dimensional ultrasound image data groups in a time series generated by scanning the subject P on a plurality of scanning sections to generate a plurality of pieces of two-dimensional analysis image data. An input unit 130 receives setting of the landmark on each of the plurality of pieces of two-dimensional ultrasound image data constituting a plurality of two-dimensional ultrasound image data groups.

Figure 25A:
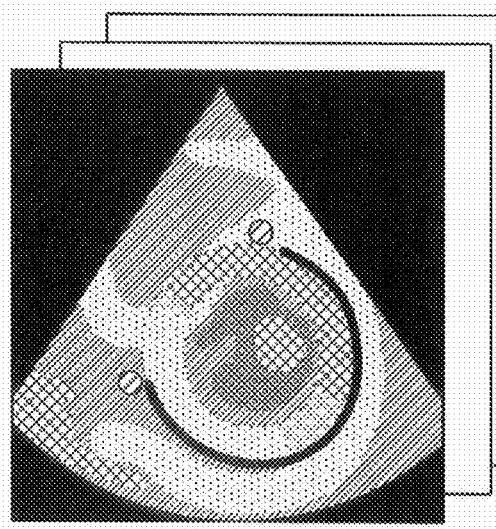
FIG. 25A, FIG. 25B, FIG. 25C and FIG. 26 are views for explaining the third embodiment.

As illustrated in FIG. 25A, the input unit 130 receives setting of a landmark formed of two points and a line on "two-dimensional ultrasound image data corresponding to two-dimensional end-systolic analysis image data at the C3 level", "two-dimensional ultrasound image data corresponding to two-dimensional end-systolic analysis image data at the C5 level", and "two-dimensional ultrasound image data corresponding to two-dimensional end-systolic analysis image data at the C7 level", for example.

The output unit 157a adds the position information of the landmark to each of a plurality of pieces of two-dimensional analysis result data corresponding to the plurality of pieces of two-dimensional analysis image data used for setting of the landmark. The output unit 157a further adds relative position information indicating a relative positional relation among the plurality of pieces of two-dimensional analysis result data based on the position information (three-dimensional position information) acquired by the position sensor 160. The output unit 157a outputs data obtained by adding the information of the position of the landmark and further adding the relative position information to the plurality of pieces of two-dimensional analysis result data as output data.

Figure 25B:
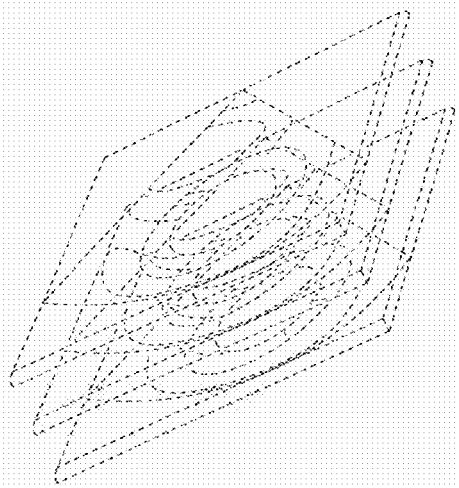

An acquiring unit 221a according to the third embodiment arranges the plurality of pieces of two-dimensional analysis result data in the three-dimensional capturing space as illustrated in FIG. 25B, based on the relative position information read from the output data.

Figure 25C:
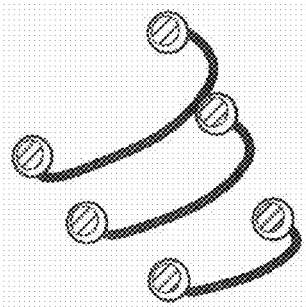

In the third embodiment, the landmark in each two-dimensional analysis result data is projected onto first-direction X-ray image data and second-direction X-ray image data, for example. Also in the third embodiment, the operator performs an operation such that the landmark projection position coincides with the coronary vein depicted in the X-ray contrast enhanced image data. As a result, the position of the landmark in the three-dimensional capturing space is modified on each of the three sections as illustrated in FIG. 25C. Along with this, the positions of the respective pieces of two-dimensional analysis image data in the three-dimensional capturing space are modified. Also in the third embodiment, the operation of the operator may possibly deform the plurality of pieces of two-dimensional analysis image data. Also in the third embodiment, the acquiring unit 221a may acquire the three-dimensional position information of the landmark based on a piece of X-ray image data captured in one direction and the landmark projection positions on the respective three sections.

Also in the third embodiment, a display unit 223 displays image data in which the plurality of pieces of two-dimensional analysis image data are superimposed on the X-ray image data of the heart by projecting the plurality of pieces of two-dimensional analysis image data rearranged in the three-dimensional capturing space in a direction desired by the doctor. In the third embodiment, the projection images of respective pieces of two-dimensional synthetic data are superimposed and displayed in a manner aligned with the X-ray image data, for example. In the third embodiment, the image data superimposed and displayed in a manner aligned with the X-ray image data may be ultrasound image data on a plurality of short-axis planes including a short-axis plane of the asynchronous area, for example.

The third embodiment may be embodied by a modification described below. In the present modification, the output unit 157a arranges the plurality of pieces of two-dimensional analysis result data corresponding to the respective pieces of two-dimensional analysis data in the three-dimensional space based on the position information acquired by the position sensor 160, thereby generating three-dimensional analysis result data. The output unit 157a outputs data obtained by adding the information of the position of the landmark in the three-dimensional analysis result data to the three-dimensional analysis result data as output data. The acquiring unit 221a arranges the three-dimensional analysis result data in the three-dimensional capturing space. In the modification, processing performed after the three-dimensional analysis result data is arranged is the same as that in the first embodiment.

Figure 26:
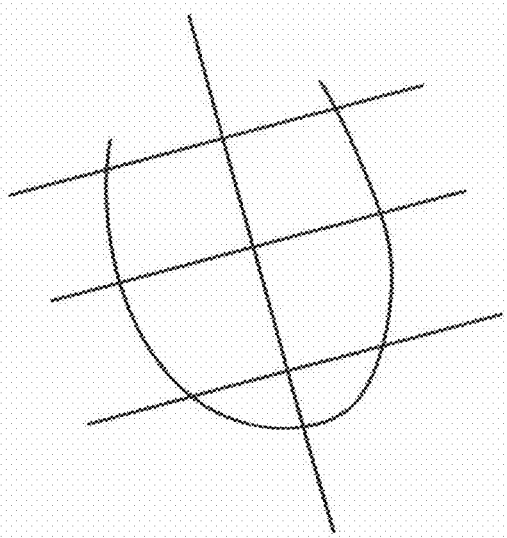

In the third embodiment, the section on which the two-dimensional ultrasonic scanning is performed is not limited to the short-axis sections. In the third embodiment, the section on which the two-dimensional ultrasonic scanning is performed may be a long-axis section including the three short-axis sections and the cardiac apex as illustrated in FIG. 26, for example. In such a case, a point corresponding to the cardiac apex can be set as a landmark in the two-dimensional ultrasound image data on the long-axis section. The contents described in the first embodiment are also applied to the third embodiment as much as possible except that the analysis image data is a plurality of pieces of two-dimensional data.

As described above, because the third embodiment uses a plurality of pieces of two-dimensional analysis image data, the doctor can check a wide range of the asynchronous area compared with the case where a piece of two-dimensional analysis image data is used. Thus, the third embodiment enables the doctor to place the electrode into a position at which a large therapeutic effect is achieved compared with the second embodiment.

The first to the third embodiments describe the case where the input unit 130 receives a plurality of landmarks each represented by a point or a line and the display unit 223 projects and displays the points and the lines representing the landmarks on X-ray image data. In the first to the third embodiments, when displaying a plurality of landmark projection positions onto which a plurality of landmarks received by the input unit 130 are projected, the display unit 223 may cause a display format of the landmarks to vary so as to make the plurality of landmarks distinguishable from one another.

Based on the control of the acquiring unit 221a, the display unit 223 displays at least one of characters, symbols, marks, and subscripts varying depending on the landmarks beside the landmarks each of which being represented by a point or a line so as to make the landmarks distinguishable from one another, for example. Alternatively, based on the control of the acquiring unit 221a, the display unit 223 displays the landmarks such that at least one of the sizes, the shapes, the densities, and the colors of the landmarks vary, thereby making the landmarks distinguishable from one another, for example. When projecting and displaying a plurality of points, the display unit 223 displays the points such that at least one of the sizes, the shapes, the densities, and the colors of the points vary, for example.

As a result, the difference in the display format can facilitate the operator's operation for distinguishing the landmarks and associating the landmarks with the respective landmark projection positions. The variations in the display format are automatically created based on the control of the acquiring unit 221a. Alternatively, when inputting points and lines as the plurality of landmarks with the input unit 130, the operator may input characters, such as "T" and "L", symbols, and marks beside the landmarks or depict the landmarks so as to make the plurality of landmarks distinguishable from one another, thereby creating the variations.

The processing of each unit described in the first to the third embodiments may be performed by the image processing apparatus 400. A part or all of the generation of the analysis image data, the reception of setting of the landmark, the outputting of the output data, and the acquisition of the three-dimensional position information of the landmark may be performed by the image processing apparatus 400, for example. The superimposed image of the analysis image data and the X-ray image data thus aligned may be generated by the image processing apparatus 400. In other words, a specific form of distribution and integration of the processing units described in the first to the third embodiments is not limited to that illustrated in the drawings. All or a part of the processing units may be functionally or physically distributed and integrated in arbitrary units depending on various types of loads and usage.

The first to the third embodiments describe the case where the first medical image data is ultrasound image data. The contents described in the first to the third embodiments are applicable to any case as long as the first three-dimensional medical image data is medical image data in which the heart serving as the certain tissue is depicted and the motion of the heart is analyzable. The contents described in the first to the third embodiments, for example, are applicable to the case where the first medical image data is X-ray CT image data captured at a time phase when the contrast of the myocardium is enhanced or MRI image data captured at a time phase when the contrast of the myocardium is enhanced.

The first to the third embodiments describe the case where alignment of the X-ray image data and the ultrasound image data is performed by setting a landmark at a position, in the ultrasound image data, corresponding to the specific tissue that is identifiable in the X-ray image data. In other words, the first to the third embodiments describe the case where the second medical image data is X-ray image data. The image processing method described in the first to the third embodiments is also applicable to the case where the target to be aligned with the first medical image data is another type of medical image data different from X-ray image data. In other words, the image processing method described in the first to the third embodiments is applicable to any case as long as the second medical image data is medical image data visualizing the specific tissue. The second medical image data is X-ray computed tomography (CT) image data or magnetic resonance imaging (MRI) image data, for example. In such a case, the image processing system receives setting of a landmark at a position, in the ultrasound image data in which the certain tissue of the subject is depicted, corresponding to the specific tissue that is identifiable in a second type of medical image data. The image processing system outputs data including the information of the position of the landmark in the ultrasound image data as output data. The image processing system acquires the three-dimensional position information of the landmark in the three-dimensional capturing space based on the position of the specific tissue in a plurality of pieces of the second type of medical image data obtained by capturing the certain tissue of the subject in a plurality of directions and on the landmark projection position obtained by arranging the position of the landmark read from the output data in the three-dimensional capturing space of the plurality of pieces of the second type of medical image data and projecting the position of the landmark onto the plurality of pieces of the second type of medical image data. The image processing system displays image data obtained by superimposing analysis image data generated by analyzing the ultrasound image data on the second type of medical image data of the certain tissue based on the three-dimensional position information of the landmark. This processing makes it possible to identify the area specified in an ultrasonic diagnosis in the second type of medical image data.

The image processing method described in the first to the third embodiments can be realized by a computer, such as a personal computer and a workstation, executing an image processing program prepared in advance. The image processing program may be distributed over a network such as the Internet. Furthermore, the image processing program may be recorded in a computer-readable recording medium, such as a hard disk, a flexible disk (FD), a compact disc read-only memory (CD-ROM), a magneto-optical disk (MO), and a digital versatile disk (DVD), and executed by a computer reading the image processing program from the recording medium.

As described above, the first to the third embodiments can identify an area specified in an ultrasonic diagnosis under X-ray fluoroscopic guidance.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system, comprising:
an input device that receives setting of a landmark in first medical image data obtained by capturing a certain tissue of a subject, at a position corresponding to a specific tissue identifiable in one or a plurality of pieces of second medical image data, the first medical image data being medical image data in which the certain tissue is depicted and in which motion of the certain tissue is analyzable, and the one or the plurality of pieces of second medical image data (1) being obtained by capturing the certain tissue of the subject in one or a plurality of capturing directions, (2) corresponding to the respective capturing directions, and (3) being medical image data that visualizes the specific tissue and that is obtained by performing contrast enhanced radiography on the certain tissue or being medical image data obtained by capturing the specific tissue into which an instrument is inserted;
output circuitry that outputs data including information of a position of the landmark in the first medical image data as output data;
acquiring circuitry that receives the output data and acquires, based on the position corresponding to the specific tissue in the one or the plurality of pieces of second medical image data and based on a landmark projection position obtained by putting the position of the landmark read from the output data in a three-dimensional capturing space and by projecting the put position of the landmark onto the one or the plurality of pieces of second medical image data, three-dimensional position information of the landmark in a three-dimensional capturing space of the second medical image data; and
a display that displays image data obtained by superimposing, on the second medical image data of the certain tissue, based on the three-dimensional position information of the landmark, the first medical image data or analysis image data, the analysis image data being generated by analyzing the first medical image data.

2. The image processing system according to claim 1, wherein
the input device receives setting of the landmark at a position corresponding to the specific tissue identifiable in X-ray image data, the X-ray image data serving as the one or the plurality of pieces of second medical image data,
the acquiring circuitry puts the position of the specific tissue in the X-ray image data and the position of the landmark read from the output data in a three-dimensional capturing space of the X-ray image data, and
the display displays image data obtained by superimposing, on the X-ray image data of the certain tissue, ultrasound image data serving as the first medical image data or the analysis image data serving as the first medical image data, the analysis image data being generated by analyzing the first medical image data.

3. The image processing system according to claim 2, wherein
the display displays the landmark projection position in each of the one or the plurality of pieces of X-ray image data, and the acquiring circuitry acquires the three-dimensional position information of the landmark based on an operation for associating the landmark projection position with the position of the specific tissue in each of the one or the plurality of pieces of X-ray image data, the operation being performed by an operator who refers to the display.

4. The image processing system according to claim 3, wherein the input device receives, as the landmark in the first medical image data, at least either of three or more points, a line, or two or more points and a line.

5. The image processing system according to claim 4, wherein, when displaying a plurality of landmark projection positions onto which a plurality of landmarks received by the input device are projected, the display causes a display format to vary so as to make the plurality of landmarks distinguishable from one another.

6. The image processing system according to claim 4, wherein
the first medical image data is ultrasound image data generated by performing ultrasonic scanning on the subject,
the image processing system further includes analyzing circuitry that analyzes an ultrasound image data group in a time series generated by performing ultrasonic scanning on the subject to generate analysis image data relating to local motion in the certain tissue,
the input device receives, in the ultrasound image data constituting the ultrasound image data group, setting of the landmark,
the output circuitry uses, as analysis result data, at least either of the ultrasound image data, the analysis image data, or synthetic data of the ultrasound image data and the analysis image data, and outputs, as the output data, data obtained by adding position information of the landmark in the analysis result data to the analysis result data, and
the acquiring circuitry puts the analysis result data in the three-dimensional capturing space to acquire the landmark projection position in each of the plurality of pieces of X-ray image data.

7. The image processing system according to claim 6, wherein
the analyzing circuitry analyzes a three-dimensional ultrasound image data group in a time series to generate three-dimensional analysis image data, the three-dimensional ultrasound image data group being generated by performing three-dimensional ultrasonic scanning on the subject,
the input device receives setting of the landmark in two-dimensional image data, the two-dimensional image data being generated from three-dimensional ultrasound image data constituting the three-dimensional ultrasound image data group, and
the output circuitry uses, as the analysis result data, at least either of the three-dimensional ultrasound image data, the three-dimensional analysis image data, both the three-dimensional ultrasound image data and the three-dimensional analysis image data, or three-dimensional synthetic data of the three-dimensional ultrasound image data and the three-dimensional analysis image data.

8. The image processing system according to claim 7, wherein
the output circuitry further adds at least epicardium position information to the output data as shape information of a heart serving as the certain tissue and output the output data,
the display displays an epicardium projection position obtained by projecting the epicardium position information onto each of the plurality of pieces of X-ray image data together with the landmark projection position, and
the acquiring circuitry acquires the three-dimensional position information of the landmark further based on an operation for associating the epicardium projection position with a predetermined position of an epicardium in each of the plurality of pieces of X-ray image data, the operation being performed by the operator who refers to the display.

9. The image processing system according to claim 8, wherein the output circuitry outputs the epicardium position information as specific information, display or non-display of the specific information being switchable.

10. The image processing system according to claim 9, wherein the output circuitry outputs the specific information as information represented by a predetermined brightness value.

11. The image processing system according to claim 6, wherein
the analyzing circuitry analyzes a two-dimensional ultrasound image data group in a time series generated by performing two-dimensional ultrasonic scanning on the subject to generate two-dimensional analysis image data,
the input device receives setting of the landmark in two-dimensional ultrasound image data constituting the two-dimensional ultrasound image data group, and
the output circuitry uses, as the analysis result data, at least either of the two-dimensional ultrasound image data, the two-dimensional analysis image data, both the two-dimensional ultrasound image data and the two-dimensional analysis image data, or two-dimensional synthetic data of the two-dimensional ultrasound image data and the two-dimensional analysis image data.

12. The image processing system according to claim 11, further comprising:
a position sensor that acquires position information of an ultrasound probe, wherein
the analyzing circuitry analyzes a plurality of two-dimensional ultrasound image data groups in a time series generated by scanning the subject on a plurality of scanning sections to generate a plurality of pieces of two-dimensional analysis image data,
the input device receives setting of the landmark on each of the plurality of pieces of two-dimensional ultrasound image data constituting a plurality of two-dimensional ultrasound image data groups,
the output circuitry outputs, as the output data, data obtained by
adding the position information of the landmark to each of a plurality of pieces of two-dimensional analysis result data corresponding to the plurality of pieces of two-dimensional analysis image data, and
further adding relative position information indicating a relative positional relation among the plurality of pieces of two-dimensional analysis result data based on the position information acquired by the position sensor, and the acquiring circuitry puts the plurality of pieces of two-dimensional analysis result data in the three-dimensional capturing space based on the relative position information read from the output data.

13. The image processing system according to claim 11, further comprising:
a position sensor that acquires position information of an ultrasound probe, wherein
the analyzing circuitry analyzes a plurality of two-dimensional ultrasound image data groups in a time series generated by scanning the subject on a plurality of scanning sections to generate a plurality of pieces of two-dimensional analysis image data,
the input device receives setting of the landmark on each of the plurality of pieces of two-dimensional ultrasound image data constituting the plurality of two-dimensional ultrasound image data groups,
the output circuitry
puts the plurality of pieces of two-dimensional analysis result data corresponding to the plurality of pieces of two-dimensional analysis data in three-dimensional space based on the position information acquired by the position sensor to generate three-dimensional analysis result data, and
outputs data obtained by adding the position information of the landmark in the three-dimensional analysis result data to the three-dimensional analysis result data as the output data, and
the acquiring circuitry puts the three-dimensional analysis result data in the three-dimensional capturing space.

14. An X-ray diagnostic apparatus, comprising:
acquiring circuitry that
receives data including information of a position of a landmark in first medical image data obtained by capturing a certain tissue of a subject as output data, the first medical image data being medical image data in which the certain tissue is depicted and in which motion of the certain tissue is analyzable, and
acquires, based on a position of a specific tissue in one or a plurality of pieces of second medical image data and based on a landmark projection position being obtained by putting the position of the landmark read from the output data in a three-dimensional capturing space and by projecting the put position of the landmark onto the one or the plurality of pieces of second medical image data, three-dimensional position information of the landmark in the three-dimensional capturing space of the second medical image data, the one or the plurality of pieces of second medical image data (1) being obtained by capturing the certain tissue of the subject in one or a plurality of capturing directions, (2) corresponding to the respective capturing directions, and (3) being medical image data that visualizes the specific tissue and that is obtained by performing contrast enhanced radiography on the certain tissue or by capturing the specific tissue into which an instrument is inserted; and
a display that displays image data obtained by superimposing, on the second medical image data of the certain tissue, based on the three-dimensional position information of the landmark, the first medical image data or analysis image data, the analysis image data being generated by analyzing the first medical image data, wherein setting of the landmark at a position corresponding to the specific tissue identifiable in the second medical image data is received in the first medical image data by input circuitry.

15. An image processing method, comprising:

receiving, by an input device, setting of a landmark in first medical image data obtained by capturing a certain tissue of a subject, at a position corresponding to a specific tissue identifiable in one or a plurality of pieces of second medical image data, the first medical image data being medical image data in which the certain tissue is depicted and in which motion of the certain tissue is analyzable, and the one or the plurality of pieces of second medical image data (1) being obtained by capturing the certain tissue of the subject in one or a plurality of capturing directions, (2) corresponding to the respective capturing directions, and (3) being medical image data that visualizes the specific tissue and that is obtained by performing contrast enhanced radiography on the certain tissue or being medical image data obtained by capturing the specific tissue into which an instrument is inserted;

outputting, by output circuitry, data including information of a position of the landmark in the first medical image data as output data;

receiving, by acquiring circuitry, the output data and acquiring, by the acquiring circuitry, based on the position corresponding to the specific tissue in the one or the plurality of pieces of second medical image data and based on a landmark projection position obtained by arranging the position of the landmark read from the output data in a three-dimensional capturing space and by projecting the put position of the landmark onto the one or the plurality of pieces of second medical image data, three-dimensional position information of the landmark in a three-dimensional capturing space of the second medical image data; and displaying, by a display, image data obtained by superimposing, on the second medical image data of the certain tissue, based on the three-dimensional position information of the landmark, the first medical image data or analysis image data, the analysis image data being generated by analyzing the first medical image data.

* * * * *